(12) United States Patent
Lee et al.

(10) Patent No.: US 10,796,803 B2
(45) Date of Patent: Oct. 6, 2020

(54) METHOD FOR INTEGRATING AND PROVIDING COLLECTED DATA FROM MULTIPLE DEVICES AND ELECTRONIC DEVICE FOR IMPLEMENTING SAME

(71) Applicant: Samsung Electronics Co., Ltd., Gyeonggi-do (KR)

(72) Inventors: Kwangjo Lee, Suwon-si (KR); Hyunsu Kim, Bucheon-si (KR); Jihye Son, Suwon-si (KR); Moonbae Song, Seoul (KR); Sanghwa Lee, Seoul (KR); Woosang Lee, Suwon-si (KR); Jae-Hwan Lee, Suwon-si (KR); Jaeyoun Jeong, Seoul (KR); Bum-Sung Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/436,613

(22) Filed: Feb. 17, 2017

(65) Prior Publication Data

US 2017/0239524 A1 Aug. 24, 2017

(30) Foreign Application Priority Data

Feb. 19, 2016 (KR) .................. 10-2016-0019535

(51) Int. Cl.
*A63B 24/00* (2006.01)
*A61B 5/024* (2006.01)
(Continued)

(52) U.S. Cl.
CPC ......... *G16H 50/30* (2018.01); *A63B 24/0075* (2013.01); *G01C 22/02* (2013.01);
(Continued)

(58) Field of Classification Search
CPC .. A61B 5/1118; A61B 5/02438; G16H 40/63; A63B 24/0075; G01C 22/02;
(Continued)

(56) References Cited

U.S. PATENT DOCUMENTS 6,013,007 A * 1/2000 Root .................. A63B 24/0006
482/8
6,997,852 B2 * 2/2006 Watterson ............... H04L 67/12
482/1

(Continued)

FOREIGN PATENT DOCUMENTS

WO 2014207294 A1 12/2014

OTHER PUBLICATIONS

V.Chvatal, "A Greedy Heuristic for the Set-Covering Problem," Mathematics of Operations Research, vol. 4, No. 3, Aug. 1979, 4 pages.

(Continued)

*Primary Examiner* — Robert J Utama

(57) ABSTRACT

An electronic device includes a housing, with a display exposed through a part of the housing. The housing includes a first motion sensor to detect movement of the housing, a wireless communication circuit, a processor, and a memory that stores instructions to be executed by a processor. The instructions include generating a wireless communication channel with an external electronic device including a second motion sensor; monitoring the movement of the housing to generate first data for a first time period; receiving second data for the first time period through the wireless communication channel; calculating, as a value for the first time period, a value, smaller than the sum of a first value based on the first data and a second value based on the second data; and displaying the calculated value through a user interface displayed on the display.

5 Claims, 26 Drawing Sheets

(51) Int. Cl.
  *A61B 5/11*   (2006.01)
  *G16H 50/30*  (2018.01)
  *H04W 4/029*  (2018.01)
  *H04M 1/725*  (2006.01)
  *G16H 40/63*  (2018.01)
  *G16H 20/30*  (2018.01)
  *G01C 22/02*  (2006.01)

(52) U.S. Cl.
  CPC ............ *G16H 20/30* (2018.01); *G16H 40/63* (2018.01); *H04M 1/72522* (2013.01); *H04W 4/029* (2018.02); *A61B 5/02438* (2013.01); *A61B 5/1112* (2013.01); *A61B 5/1118* (2013.01); *H04M 1/7253* (2013.01); *H04M 1/72572* (2013.01); *H04M 2250/12* (2013.01)

(58) Field of Classification Search
  CPC ............ H04M 1/7253; H04M 1/72572; G06F 19/3481; G01P 13/00
  See application file for complete search history.

(56) References Cited

U.S. PATENT DOCUMENTS

| | | | |
|---|---|---|---|
| 7,489,979 B2 * | 2/2009 | Rosenberg | G06F 3/017 700/94 |
| 7,698,061 B2 * | 4/2010 | Singh | G01C 21/3484 348/211.3 |
| 7,827,000 B2 * | 11/2010 | Stirling | A61B 5/1038 702/141 |
| 8,676,541 B2 * | 3/2014 | Schrock | A43B 3/00 702/188 |
| 8,740,751 B2 * | 6/2014 | Shum | A61B 5/11 482/1 |
| 8,762,101 B2 | 6/2014 | Yuen et al. | |
| 8,936,552 B2 * | 1/2015 | Kateraas | A61B 5/02055 600/301 |
| 9,037,199 B1 | 5/2015 | Stogaitis et al. | |
| 9,125,015 B2 | 9/2015 | Pennanen et al. | |
| 9,215,290 B2 | 12/2015 | Yuen et al. | |
| 9,279,734 B2 * | 3/2016 | Walker | G01L 1/2206 |
| 9,289,674 B2 * | 3/2016 | Winsper | G06F 19/3481 |
| 9,409,052 B2 * | 8/2016 | Werner | A63B 24/0021 |
| 9,672,482 B2 * | 6/2017 | Rubin | G06Q 10/063114 |
| 9,723,381 B2 * | 8/2017 | Swanson | H04Q 9/00 |
| 2002/0151810 A1 * | 10/2002 | Wong | A61B 5/222 600/520 |
| 2004/0046692 A1 | 3/2004 | Robson et al. | |
| 2011/0152637 A1 * | 6/2011 | Kateraas | A61B 5/02055 600/301 |
| 2011/0159469 A1 * | 6/2011 | Hwang | A61B 5/222 434/247 |
| 2013/0325392 A1 | 12/2013 | Takahashi | |
| 2013/0325394 A1 * | 12/2013 | Yuen | H04W 4/023 702/150 |
| 2014/0163927 A1 * | 6/2014 | Molettiere | A61B 5/0002 702/189 |
| 2014/0278139 A1 | 9/2014 | Hong et al. | |
| 2015/0042468 A1 | 2/2015 | White et al. | |
| 2015/0100245 A1 | 4/2015 | Huang et al. | |
| 2015/0285659 A1 | 10/2015 | Curtis et al. | |
| 2016/0253142 A1 * | 9/2016 | Choi | G06F 3/1423 345/1.3 |
| 2016/0255187 A1 * | 9/2016 | Song | H04M 9/082 455/418 |
| 2016/0313963 A1 * | 10/2016 | Kang | G06F 3/011 |
| 2017/0041769 A1 * | 2/2017 | Shim | H04W 4/12 |

OTHER PUBLICATIONS

Foreign Communication from a Related Counterpart Application, PCT Application No. PCT/KR2017/001752, International Search Report dated May 23, 2017, 3 pages.
Foreign Communication from a Related Counterpart Application, PCT Application No. PCT/KR2017/001752, Written Opinion of the International Searching Authority dated May 23, 2017, 7 pages.
European Patent Office, "Supplementary European Search Report," Application No. EP17753502.8, dated Feb. 21, 2019, 13 pages.
Freedson, Patty S., et al., "Objective Monitoring of Physical Activity Using Motion Sensors and Heart Rate," Research Quarterly for Exercise and Sport, American Alliance for Health, Physical Education, Recreation and Dance, vol. 71, No. 2, Jun. 2000, 10 pages.
Communication pursuant to Article 94(3) EPC dated Feb. 14, 2020 in connection with European Patent Application No. 17 753 502.8, 11 pages.

* cited by examiner

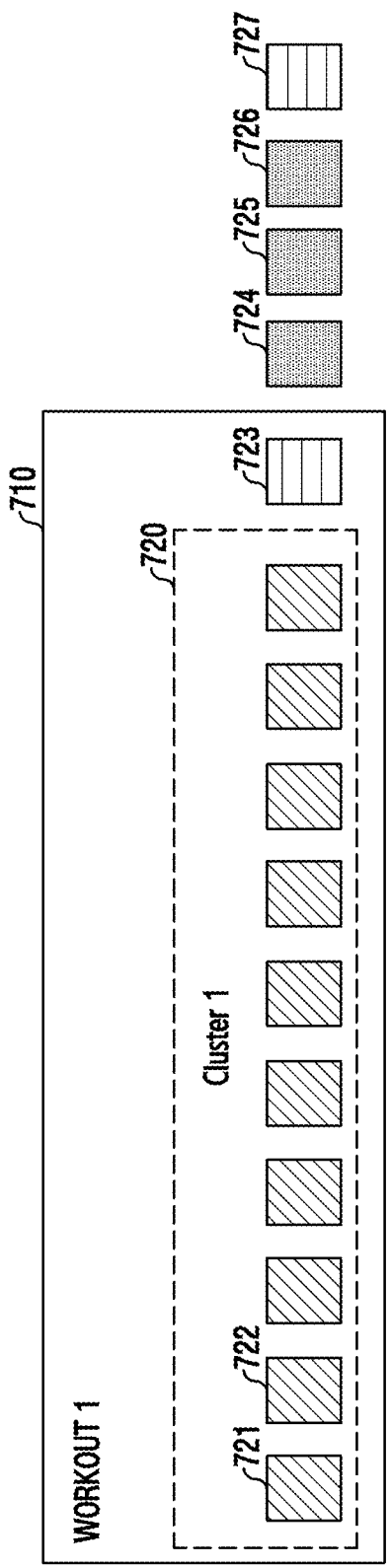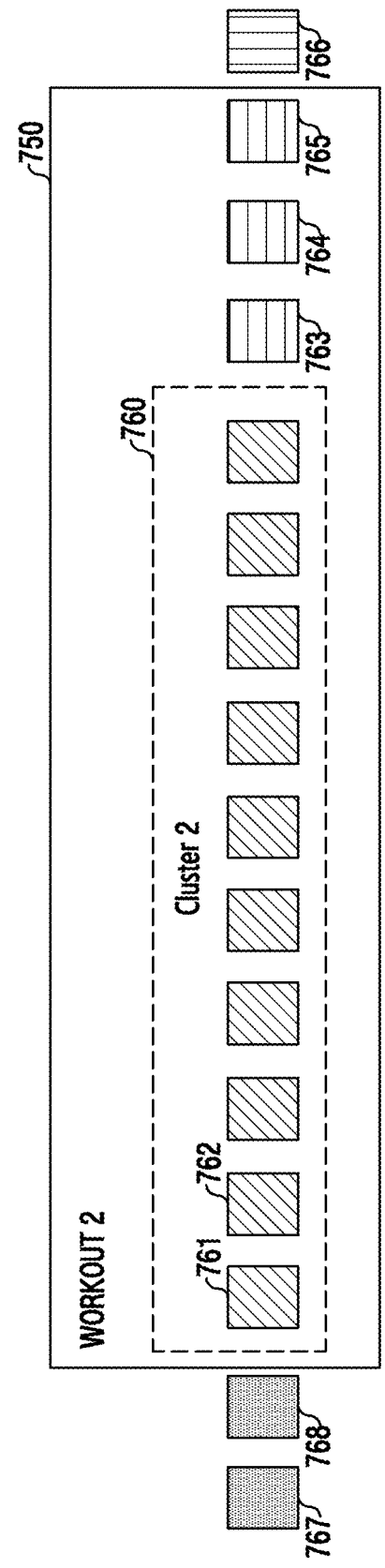

_US 10,796,803 B2_

METHOD FOR INTEGRATING AND PROVIDING COLLECTED DATA FROM MULTIPLE DEVICES AND ELECTRONIC DEVICE FOR IMPLEMENTING SAME

CROSS-REFERENCE TO RELATED APPLICATION(S) AND CLAIM OF PRIORITY

The present application is related to and claims the priority under 35 U.S.C. § 119(a) to Korean Application Serial No. 10-2016-0019535, which was filed in the Korean Intellectual Property Office on Feb. 19, 2016, the entire content of which is hereby incorporated by reference.

TECHNICAL FIELD

Various embodiments relate to a method for integrating and providing collected data from multiple devices, and an electronic device for implementing the same.

BACKGROUND

Recently, with the development of a digital technology, various types of electronic devices such as a mobile communication terminal, Personal Digital Assistant (PDA), an electronic scheduler, a smart phone, a tablet Personal Computer (PC), a wearable device, and the like, have been widely used. The electronic device has various functions such as a voice call, message transmission like a Short Message Service (SMS)/Multimedia Message Service (MMS), a video call, electronic organizer, photography, email transmission/reception, broadcast reproduction, Internet, music reproduction, schedule management, Social Networking Service (SNS), messenger, dictionary, game, and the like.

As interests in health increase, wearable devices that measure user activity, or applications that show the measured user activity are actively being developed. The wearable devices may also widely be used for medical services in the future. Since the conventional user activity display technology usually uses a single device (e.g., a wearable device) to display, it cannot provide a seamless user experience using a plurality of devices when a user uses the plurality of devices.

SUMMARY

To address the above-discussed deficiencies, it is a primary object to provide a method and apparatus that can provide a user interface or a user experience, which can analyze health related data collected from one or more electronic devices so as to find a meaningful active interval for the user, and allow the user to intuitively determine data characteristics according to the active interval.

An electronic device according to various embodiments includes: a housing; a display exposed through a part of the housing; a first motion sensor disposed within the housing and configured to detect the movement of the housing; a wireless communication circuit disposed within the housing; a processor disposed within the housing and electrically connected to the display, the first motion sensor, and the wireless communication circuit; and a memory electrically connected to the processor, wherein the memory stores instructions which, when executed by a processor, cause the processor to perform operations including: generating a wireless communication channel with an external electronic device including a second motion sensor, using the wireless communication circuit; monitoring the movement of the housing using the first motion sensor, so as to generate first data for a first time period; receiving second data acquired for the first time period through the wireless communication channel, using the second motion sensor; calculating, as a value for the first time period, a value smaller than the sum of a first value based on the first data and a second value based on the second data; and displaying the calculated value through a user interface displayed on the display.

An electronic device according to various embodiments includes: a housing; a display exposed through a part of the housing; a motion sensor disposed within the housing and configured to detect the movement of the housing; a wireless communication circuit disposed within the housing; a processor disposed within the housing and electrically connected to the display, the motion sensor, and the wireless communication circuit; and a memory electrically connected to the processor, wherein the memory stores instructions which, when executed by a processor, cause the processor to perform operations including: monitoring the movement of the housing using the motion sensor so as to generate first data for a first time period; determining a first attribute of the movement during a first session of the first time period, using a first portion of the first data; determining a second attribute of the movement during a second session of the first time period, using a second portion of the first data; selecting one of the first attribute and the second attribute; and displaying at least one of an image, a text, or a symbol representing the selected attribute through a user interface displayed on the display.

An electronic device according to various embodiments includes a memory, a display, a communication interface, and a processor functionally connected to the memory, the display, or the communication interface, wherein the processor may be configured to acquire, through the communication interface, health related data collected from an external device, correct the acquired data per unit time, analyze the corrected data to extract activity information, store the extracted activity information in the memory, and display a user interface including the activity information on the display in response to a user request.

An operation method for an electronic device according to various embodiments may include: acquiring health related data; correcting the acquired data per unit time; analyzing the corrected data to extract activity information; and displaying a user interface including the activity information in response to a user request.

According to various embodiments, a user interface or user experience can be provided, which can analyze health related data collected from one or more electronic devices so as to find a meaningful active interval for the user, and allow the user to intuitively determine data characteristics according to the active interval.

According to various embodiments, health related data collected from a plurality of electronic devices may be integrated, so as to provide a seamless user experience for the number of steps, activity information, or non-activity information of the user.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 7A and 7B illustrate an example of data analysis according to various embodiments;

FIG. 22A to FIG. 24B illustrate an example of correcting an icon in an active area based on a threshold according to various embodiments.

DETAILED DESCRIPTION

Figure 1:
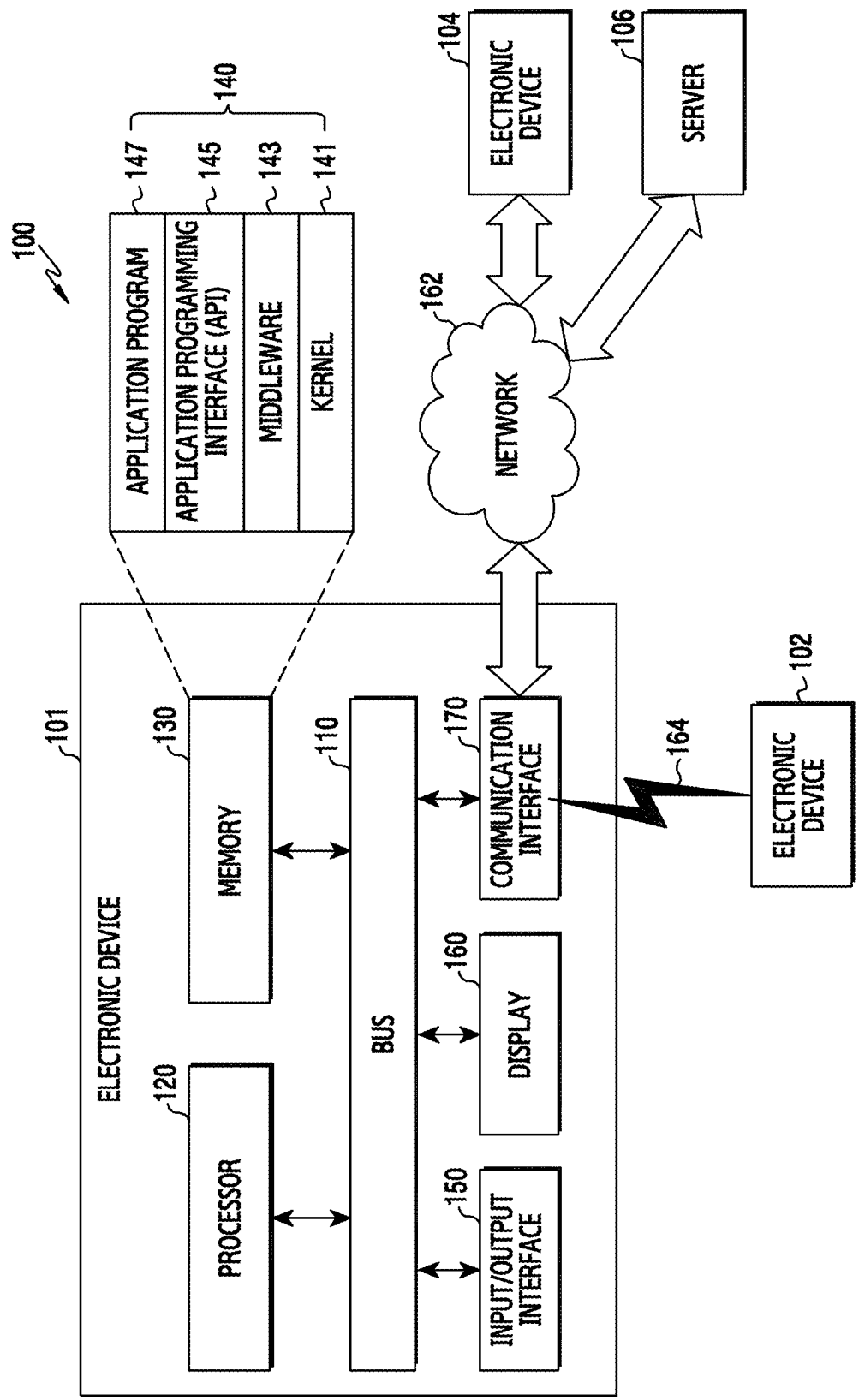
FIG. 1 illustrates an electronic device within a network environment according to various embodiments.

FIGS. 1 through 26C, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements. As used herein, the expression "have", "may have", "include", or "may include" refers to the existence of a corresponding feature (e.g., numeral, function, operation, or constituent element such as component), and does not exclude one or more additional features. In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B. The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit). According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., SAMSUNG HOMESYNC™, APPLE TV®, or GOOGLE TV®), a game console (e.g., XBOX® and PLAYSTATION®), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology. Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments of the present disclosure.

An electronic device 101 within a network environment 100, according to various embodiments, will be described with reference to FIG. 1. The electronic device 101 may include a bus 110, a processor 120, a memory 130, an input/output interface 150, a display 160, and a communication interface 170. According to an embodiment of the present disclosure, the electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include one or more of a Central Processing Unit (CPU), an Application Processor (AP), and a Communication Processor (CP). The processor 120 may carry out, for example, calculation or data processing relating to control and/or communication of at least one other component of the electronic device 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data. Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150, for example, may function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a MicroElectroMechanical Systems (MEMS) display, and an electronic paper display. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106). The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short range communication 164.

The short-range communication 164 may include at least one of, for example, Wi-Fi, Bluetooth, Near Field Communication (NFC), and Global Navigation Satellite System (GNSS). GNSS may include, for example, at least one of global positioning system (GPS), global navigation satellite system (GLONASS), Beidou Navigation satellite system (BEIDOU) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS). The network 162 may include at least one of a telecommunication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. According to various embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

Figure 2:
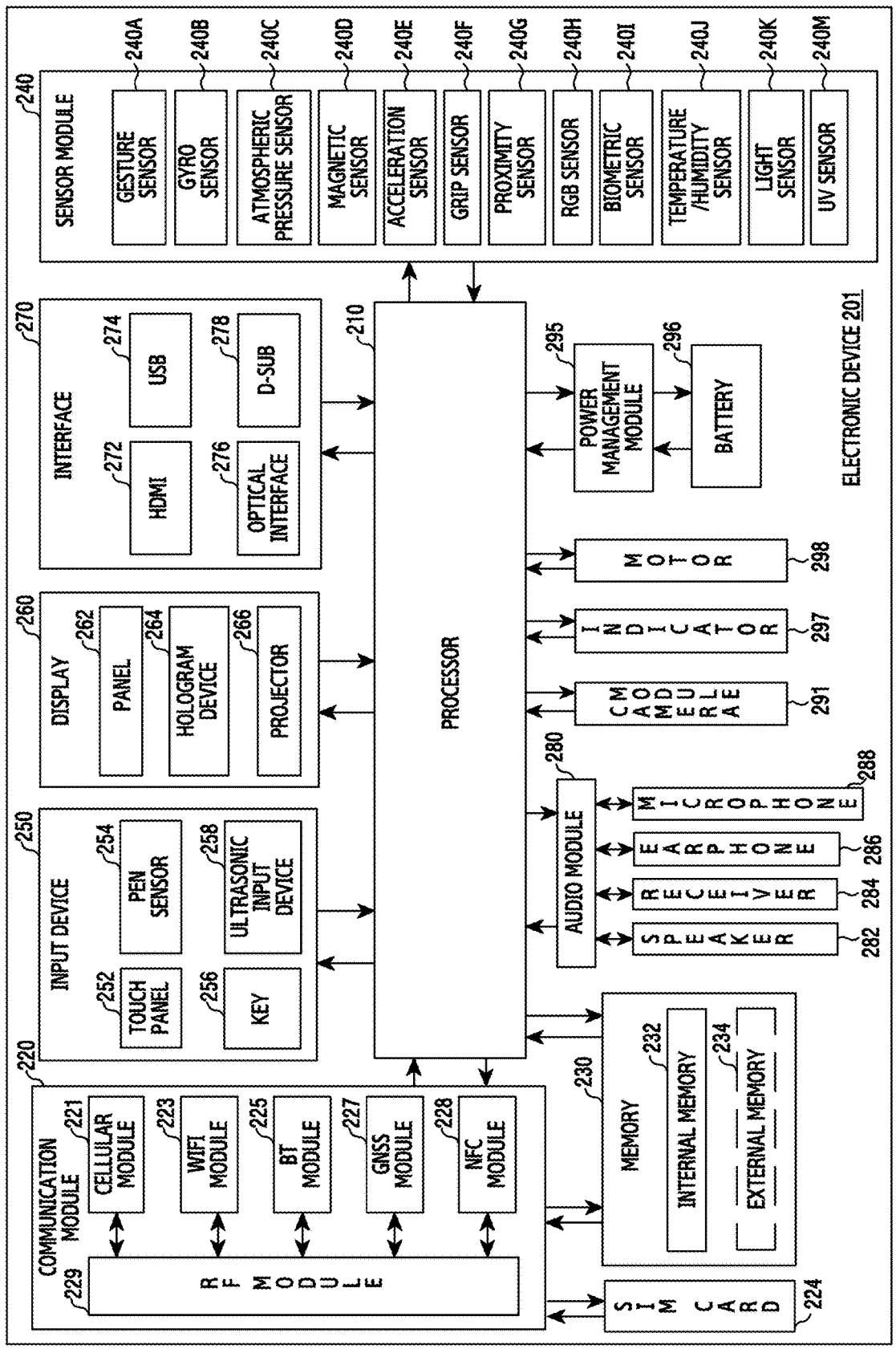
FIG. 2 illustrates a configuration of an electronic device according to various embodiments.

FIG. 2 illustrates an electronic device according to various embodiments of the present disclosure.

The electronic device 201 may include, for example, all or a part of the electronic device 101 shown in FIG. 1. The electronic device 201 may include one or more processors 210 (e.g., Application Processors (AP)), a communication module 220, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include, for example, a cellular module 221, a Wi-Fi module 223, a BT module 225, a GNSS module 227 (e.g., a GPS module 227, a Glonass module, a Beidou module, or a Galileo module), an NFC module 228, and a Radio Frequency (RF) module 229. The cellular module 221, for example, may provide a voice call, a video call, a text message service, or an Internet service through a communication network. According to an embodiment of the present disclosure, the cellular module 221 may distinguish and authenticate the electronic device 201 in a communication network using a subscriber identification module (e.g: SIM card) 224 (for example, the SIM card). According to an embodiment of the present disclosure, the cellular module 221 may perform at least some of the functions that the AP 210 may provide. According to an embodiment of the present disclosure, the cellular module 221 may include a communication processor (CP).

For example, each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one Integrated Chip (IC) or IC package. The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the Wi-Fi module 223, the BT module 225, the GNSS module 227, and the NFC module 228 may transmit/receive an RF signal through a separate RF module. The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like). The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMediaCard (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user. The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-subminiature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288. The camera module 291 is, for example, a device which may photograph a still image and a video. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or MEDIA-FLO™.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
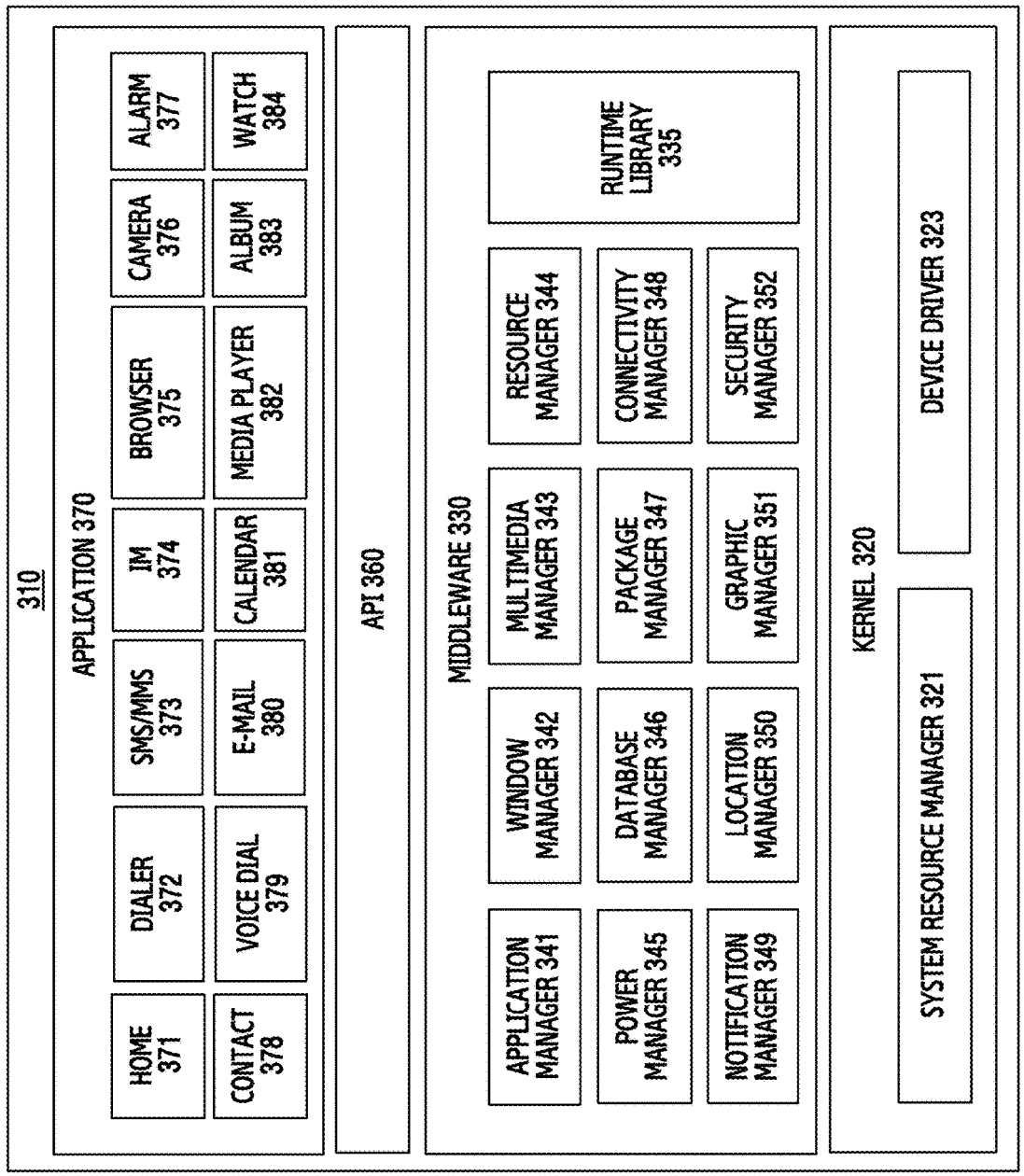
FIG. 3 illustrates a program module according to various embodiments.

FIG. 3 illustrates a program module according to various embodiments of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, ANDROID®, iOS®, WINDOWS®, SYMBIAN®, TIZEN®, SAMSUNG BADA®, or the like. The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

For example, the middleware 330 may provide a function required in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) may include at least one of a run time library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format required for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like required for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as WI-FI® or BLUETOOTH®. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions required for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, contacts 378, a voice dial 379, an email 380, a calendar 381, a media player 382, an album 383, a clock 384, health care (e.g., measuring exercise quantity or blood sugar), or environment information (e.g., providing atmospheric pressure, humidity, or temperature information).

According to an embodiment of the present disclosure, the applications 370 may include an application (hereinafter, referred to as an "information exchange application" for convenience of description) that supports exchanging information between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (e.g., the electronic device 102 or 104), notification information generated from other applications of the electronic device 101 (e.g., an SMS/MMS application, an e-mail application, a health management application, or an environmental information application). Further, the notification relay application may receive notification information from, for example, an external electronic device and provide the received notification information to a user.

The device management application may manage (e.g., install, delete, or update), for example, at least one function of an external electronic device (e.g., the electronic device 102 or 104) communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance or the like) designated according to an external electronic device (e.g., attributes of the electronic device 102 or 104). According to an embodiment of the present disclosure, the applications 370 may include an application received from an external electronic device (e.g., the server 106, or the electronic device 102 or 104). According to an embodiment of the present disclosure, the applications 370 may include a preloaded application or a third party application that may be downloaded from a server. The names of the components of the program module 310 of the illustrated embodiment of the present disclosure may change according to the type of operating system.

According to various embodiments, at least a part of the programming module 310 may be implemented in software, firmware, hardware, or a combination of two or more thereof. At least some of the program module 310 may be implemented (e.g., executed) by, for example, the processor (e.g., the processor 210). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter. According to various embodiments, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable recoding media may be, for example, the memory 130.

Figure 4:
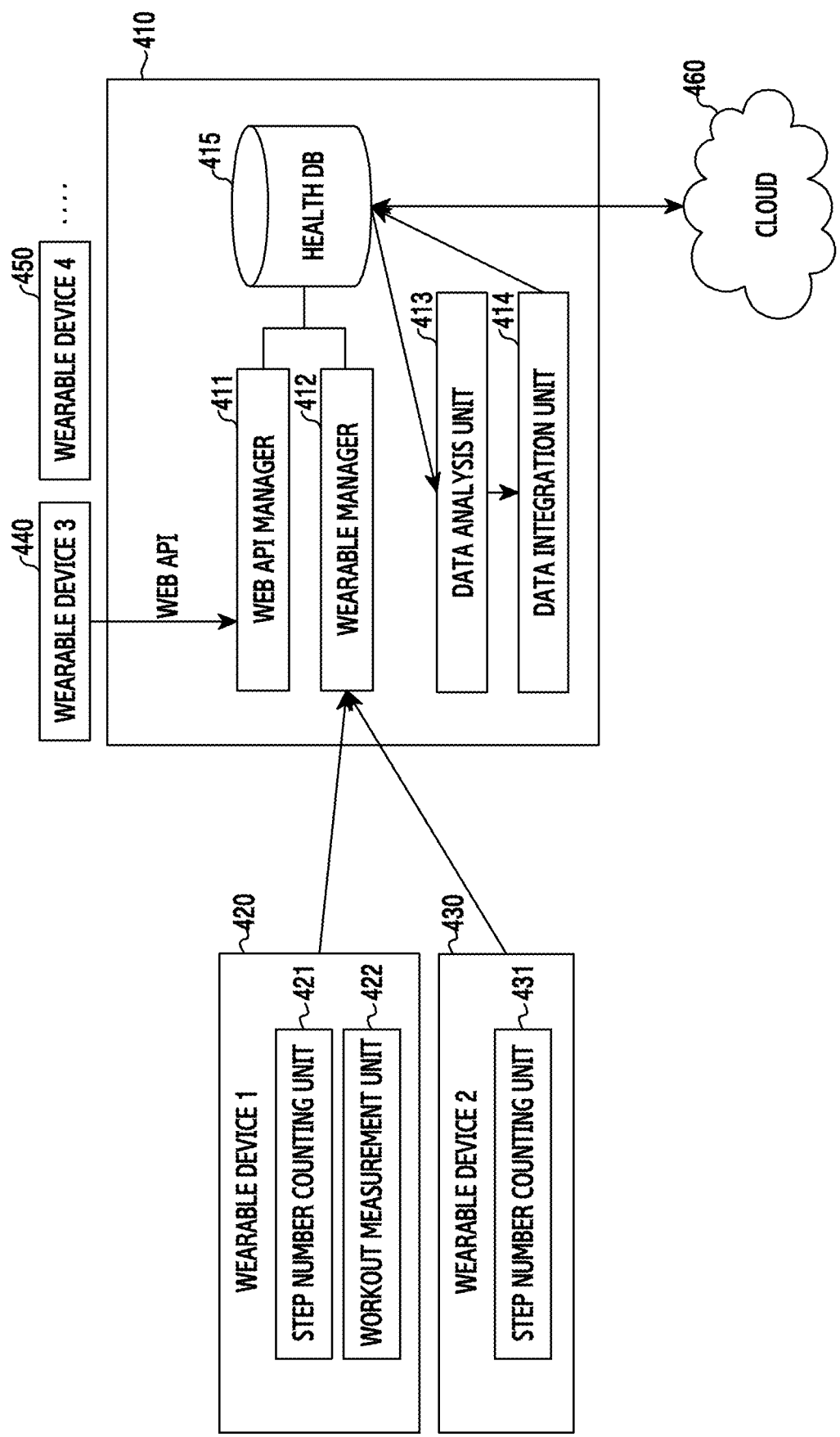
FIG. 4 illustrates the configuration of an electronic device and a wearable device according to various embodiments.

FIG. 4 illustrates the configuration of an electronic device and a wearable device according to various embodiments.

Referring to FIG. 4, an electronic device 410 may include a web API manager 411, a wearable manager 412, a data analysis unit 413, a data integration unit 414, and a health DB 415.

The web API manager 411 may receive health related data, which is collected from a wearable device 3 440 or a wearable device 4 450, using a protocol released in the form of a web application programming interface (API). The wearable manager 412 may receive the health related data, which is collected from a wearable device 1 420 or a wearable device 2 430, using the communication protocol defined for the wearable device 1 420 or the wearable device 2 430. Here, the received data may be health related data (e.g., number of steps, cycling, swimming, sleep, etc.) measured or collected by the wearable device 1 420 to the wearable device 4 450.

The received data may be stored in a health database (DB) 415. The received data is measured or collected by one or more wearable devices, and the data may be individually provided to each device, but one piece of integrated data may be provided thereto. The health DB 415 may store data received for each device, or may integrate data received from a plurality of devices and store the same. The data stored in the health DB 415 may be synchronized with a cloud 460.

The data analysis unit 413 may analyze the received data. For example, the data analysis unit 413 may analyze the received data and classify the same depending on activity types. Here, the activity type may include a first activity type for the number of steps, a second activity type for an activity (e.g., workout), and a third activity type for non-activity. The non-activity may mean a stationary state such as sleeping, sitting, and the like without walking or activity (e.g., cycling, swimming, etc.). Alternatively, the non-activity may mean that there is no detection.

For example, the wearable device 1 420 may collect data for the number of steps and activities, the wearable device 2 430 may collect data for the number of steps, the wearable device 3 440 may collect data for the number of steps and activities, and the wearable device 4 450 may collect data on the number of steps. The data analysis unit 413 may classify the data depending on the activity types in order to integrate the data received from the wearable device 1 420 to the wearable device 4 450 into one piece of data.

The data integration unit 414 may integrate the data classified depending on activity types. For example, the data integration unit 414 may integrate respective data for the number of steps, an activity, and a non-activity. The data integration unit 414 may store the integrated data in the health DB 415.

According to various embodiments, the wearable device 1 420 may include a step number counting unit 421 for measuring the number of steps, and a workout measurement unit 422 for measuring activity. The wearable device 2 430 may include a step number counting unit 431 for measuring the number of steps. According to various embodiments, the wearable device 1 420 to the wearable device 4 450 may have different unit time for storing the measured data. For example, the wearable device 1 420 and the wearable device 3 440 may store data in a unit of 5 minutes, and the wearable device 2 430 and the wearable device 4 450 may store data in a unit of 10 minutes.

Figure 5:
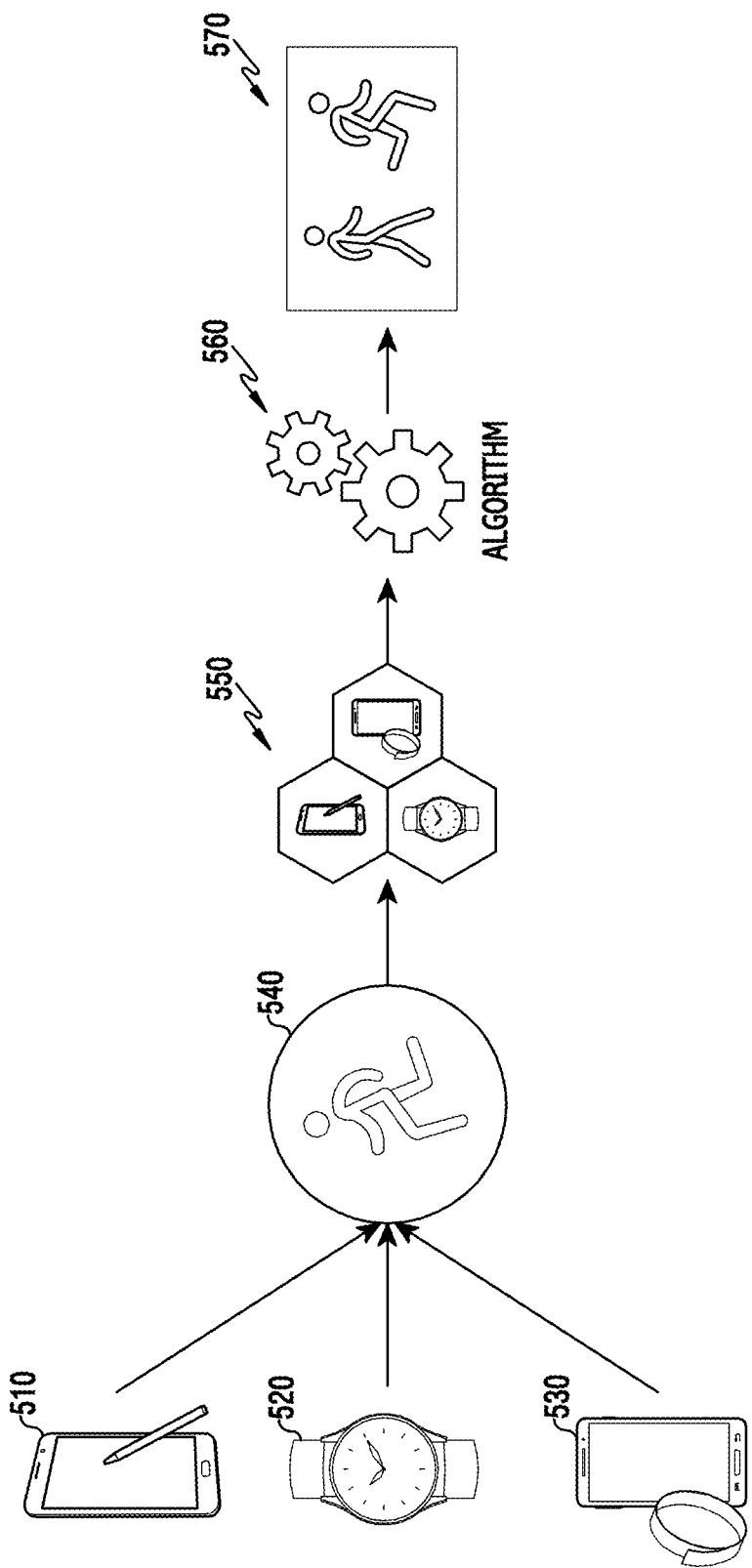
FIG. 5 illustrates an example of a health related data flow according to various embodiments.

FIG. 5 illustrates an example of a health related data flow according to various embodiments.

Referring to FIG. 5, data 540, which is collected from an electronic device 510, a wearable device 520, and an application 530, respectively, may be stored in the health DB 415. The data analysis unit 413 may perform an analysis of data (indicated by reference numeral 550) stored in the health DB 415. The data integration unit 414 may perform integration of data based on the result of analysis. The data integration unit 414 may apply an algorithm 560 to the integrated data to correct the data. The corrected data 570 is for the number of steps, activity, and non-activity, and may be provided through a user interface.

The electronic device described below may be at least one of the electronic device 101 of FIG. 1, the electronic device 201 of FIG. 2, or the electronic device 410 of FIG. 4. In the following, for the convenience of explanation, an electronic device is described as the electronic device 101 of FIG. 1, but the electronic device is not limited to the description thereof.

An electronic device according to various embodiments includes: a housing; a display exposed through a part of the housing; a first motion sensor disposed within the housing and configured to detect the movement of the housing; a wireless communication circuit disposed within the housing; a processor disposed within the housing and electrically connected to the display, the first motion sensor, and the wireless communication circuit; and a memory electrically connected to the processor, wherein the memory stores instructions which, when executed by a processor, cause the processor to perform operations including: generating a wireless communication channel with an external electronic device including a second motion sensor, using the wireless communication circuit; monitoring the movement of the housing using the first motion sensor so as to generate first data for a first time period; receiving second data acquired for the first time period through the wireless communication channel, using the second motion sensor; calculating, as a value for the first time period, a value smaller than the sum of a first value based on the first data and a second value based on the second data; and displaying the calculated value through a user interface displayed on the display.

According to an embodiment, the instructions cause the processor to display the calculated value after the first time period through the user interface when the electronic device and the external electronic device are being worn or carried by a user.

An electronic device according to various embodiments includes: a housing; a display exposed through a part of the housing; a motion sensor disposed within the housing and configured to detect the movement of the housing; a wireless communication circuit disposed within the housing; a processor disposed within the housing and electrically connected to the display, the motion sensor, and the wireless communication circuit; and a memory electrically connected to the processor, wherein the memory stores instructions which, when executed by a processor, cause the processor to perform operations including: monitoring the movement of the housing using the motion sensor so as to generate first data for a first time period; determining a first attribute of the movement during a first session of the first time period, using a first portion of the first data; determining a second attribute of the movement during a second session of the first time period, using a second portion of the first data; selecting one of the first attribute and the second attribute; and displaying at least one of an image, text, or a symbol representing the selected attribute through a user interface displayed on the display.

The instructions according to an embodiment cause the processor to display, through the user interface, a map associated with locations where the housing has been located for the first time period, and to display at least one of the image, the text, or the symbol on the map in a superposed manner.

The instructions according to an embodiment may cause the processor to receive second data acquired for the first time period from an external electronic device including a motion sensor through the wireless communication circuit; calculate, as a value for the first time period, a value smaller than the sum of a first value based on the first data and a second value based on the second data; and display the calculated value through a user interface displayed on the display.

An electronic device according to various embodiments includes a memory, a display, a communication interface, and a processor functionally connected to the memory, the display, or the communication interface, wherein the processor may be configured to acquire, through the communication interface, health related data collected from an external device, correct the acquired data per unit time, analyze the corrected data to extract activity information, store the extracted activity information in the memory, and display, on the display, a user interface including the activity information in response to a user request.

The processor according to an embodiment may be configured to correct the acquired data based on a time unit for storing data of the electronic device.

The processor according to an embodiment may be configured to analyze data acquired from the external device and data acquired using a sensor module of the electronic device, so as to classify the data depending on activity types, and integrate the data depending on the activity types.

The processor according to an embodiment may be configured to integrate data based on a priority of at least one of time, an activity type, a workout type, and a device.

The processor according to an embodiment may be configured to assign different weights to at least one of the activity type, the workout type, and the device, and correct the integrated data based on the weights.

The processor according to an embodiment may be configured to classify the number of steps for each device per unit time, determine the maximum number of steps per unit time, and calculate the integrated number of steps based on the determined maximum number of steps, so as to integrate data for the number of steps.

The processor according to an embodiment may be configured to determine a workout type based on the result of data analysis, determine the start and end of the workout type, and integrate activity information for each workout type based on the priority.

The processor according to an embodiment may be configured to align inactive intervals for each time, and integrate non-active periods that do not include the activity information into one session, so as to process the integrated session as non-activity information.

The processor according to an embodiment may be configured to extract location information on the activity information, calculate an active area for activity information based on the extracted location information, calculate a distance between two adjacent active areas, and correct an icon in the active area based on the calculated distance.

The processor according to an embodiment may be configured to determine such that the icon overlap condition is satisfied when the calculated distance is less than a reference distance, and determine at least one of icons included in the adjacent two active areas.

Figure 6:
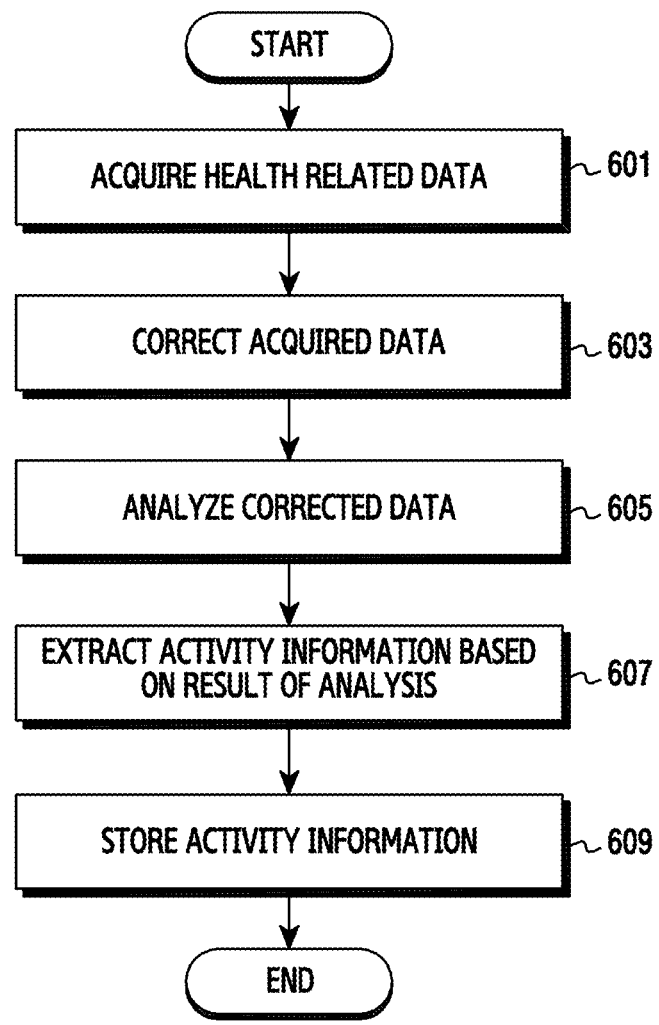
FIG. 6 illustrates an operation method for an electronic device according to various embodiments.

FIG. 6 illustrates an operation method for the electronic device according to various embodiments.

FIG. 6 illustrates an operation of extracting activity information using one piece of data. Referring to FIG. 6, in operation 601, the electronic device 101 (e.g., the processor 120) may acquire health related data. The processor 120 may receive health related data from the external device (or an external electronic device) (e.g., one of the electronic device 102, the electronic device 104, and the wearable device 1 420 to the wearable device 4 450) through the communication interface 170. Alternatively, the electronic device 101 may autonomously acquire health related data. The electronic device 101 may acquire health related data using various sensor modules (e.g., the sensor module 240 of FIG. 2). The health related data may be data collected or measured by the external device or the electronic device 101, for example, the number of steps, running, cycling, swimming, sleeping, resting, and the like. The acquired data may be stored in the memory 130. In operation 603, the electronic device 101 (for example, the processor 120) may correct the acquired data. For example, the electronic device 101 may store data in a unit of minutes, the wearable device 1 420 and wearable device 3 440 may store data in a unit of five minutes, and the wearable device 2 430 and wearable device 4 450 may store data in a unit of ten minutes. Since the unit time for storing data is different for each device, the processor 120 may divide the received data according to the unit time for data storage of the electronic device 101. For example, the processor 120 may divide the received data by a unit of one minute. In operation 601, when the electronic device 101 has autonomously acquired the data not received from the external device, the operation 603 may not be performed. In addition, examples of the unit time are only examples, and the unit time for storing data in the electronic device 101 or the external device may be 30 seconds, 3 minutes, 5 minutes, or the like.

In operation 605, the electronic device 101 (for example, the processor 120) may analyze the corrected data. For example, various clustering or pattern recognition technologies may be utilized for data analysis methods. The processor 120 may analyze the corrected data using various technologies, so as to extract an activity that is determined to be meaningful to a user. According to medical opinion, a person may be healthy if he or she can walk an average of 100 or more steps over 10 minutes. The processor 120 may analyze the received data using density-based spatial clustering of applications with noise (DBSCAN) among various clustering technologies based on the medical opinion.

According to various embodiments, the processor 120 may search for, from data divided by one minute, a cluster having a condition that the minPts of the DBSCAN is 10 steps or more and the eps is one minute, and determine whether a user's activity is walking or running based on the number of steps within the corresponding cluster. For reference, the DBSCAN has two variables, and the minPts is the minimum number of objects to be included in one cluster, and the eps may mean the distance between objects. Here, the object is the number of steps, and the distance between the objects may be one minute, which is a unit of storing data of the electronic device 101. The processor 120 may include, in one cluster, objects walking 10 or more steps from data divided by one minute. When an initial condition included in one cluster is achieved one time and data generation (e.g., generation of the number of steps) is continuously maintained, the processor 120 may maintain a state where data is included in the cluster until a termination condition occurs. For example, the initial condition may be 10 or more steps per minute, or an average of 100 or more steps for 10 minutes. The termination condition may correspond to a case where there are no detected steps or less than 10 steps per minute. Data analysis of the number of steps will be described in detail with reference to FIGS. 7A and 7B below.

In operation 607, the electronic device 101 (for example, the processor 120) may extract activity information based on the result of analysis. According to an embodiment, when the analyzed data is used for classifying walking and running, the processor 120 may compare the sum of the walking with the sum of the running so as to extract an activity that has a larger value as activity information. For example, when the sum of the walking is 1000 and the sum of the running is 400 in one cluster, the processor 120 may extract a walking time and a total number of steps as the activity information. Alternatively, when the sum of the walking is 500 and the sum of the running is 2000, the processor 120 may extract a running time and a total running distance as activity information. According to various embodiments, when it is configured such that a user may acquire location information or when a user is allowed to acquire location information, the location information on the walking distance or the running distance may be extracted as the activity information.

According to the embodiment, when the analyzed data is not used for classify walking and running, the processor 120 may determine the workout types by using the number of steps per unit time. For example, the processor 120 may determine as 'running' when the number of steps is 150 or more per minute, and determine as 'walking' when the number of steps is less than 150 per minute. The processor 120 may compare the determined sum of the walking with the sum of the running, so as to extract an activity that has a larger value as activity information.

According to an embodiment, the processor 120 may analyze the frequency of steps per unit time (e.g., one minute) so as to extract activity information. The processor 120 may calculate the speed information using the GNSS module 227, or may determine whether the activity corresponds to an outdoor activity using an ultraviolet-ray sensor. For example, the processor 120 may calculate the moving speed for 10 minutes based on a change in location information when the number of steps generated for 10 minutes is equal to or greater than a predetermined number of steps (e.g., 1000 steps). When the calculated moving speed is equal to or higher than a predetermined speed (e.g., 20 Km/h), the processor 120 may extract the cycling, the moving speed, the moving distance, and the like as activity information. Alternatively, when the calculated moving speed is within a bicycle speed range (e.g., 20 Km/h to 50 Km/h), the processor 120 may extract the cycling, the moving speed, the moving distance, and the like as activity information. For example, when the number of steps is equal to or greater than a predetermined number of steps (e.g., 100 steps) or is generated in a predetermined pattern, the processor 120 may recognize the same as the outdoor activity if the sensor value of the ultraviolet sensor is a value that can be collected outdoors.

In operation 609, the electronic device 101 (for example, the processor 120) may store the extracted activity information. The processor 120 may store the extracted activity information in the memory 130. The activity information represents information such as walking, running, or total number of steps, total running distance, etc., and may be provided through a user interface that may be easily distinguished by a user.

FIGS. 7A and 7B illustrate an example of data analysis according to various embodiments.

Referring to FIGS. 7A and 7B, the electronic device 101 (for example, the processor 120) may determine activity information based on the number of steps per unit time. For example, the processor 120 may classify health related data in a unit of one minute, and include an object, which has generated 10 steps or more per minute in a workout 1 710. The workout 1 710 may include objects (for example 721 and 722) walking average 100 steps or more for ten minutes and an object 723 walking 10 steps or more per minute. For example, if the initial condition is achieved one time and the number of steps is continuously generated, the processor 120 may include, in the cluster 1 720, the number of steps which has generated until the termination condition occurs. When the objects (for example, 721 and 722) which have generated the average 100 steps or more for 10 minutes are included in the cluster 1 720, the processor 120 may also include the object 723, which has generated 10 steps or more per minute, in the cluster 1 720.

According to an embodiment, when the average 100 steps have generated during a predetermined time unit (e.g., one minute, five minutes, 10 minutes), the processor 120 may determine the case as an initial condition that is included in one workout (or cluster). Here, the termination condition may correspond to a case where there is no detected steps or less than 10 steps per minute. For example, the processor 120 may not include, in the workout 1 710, objects (for example, 724, 725, and 726) in which there are no detected steps or the object 727 that has generated less than 10 steps.

According to various embodiments, the processor 120 may classify health related data in a unit of one minute, and if the number of steps per minute is less than a predetermined number of steps (e.g., 10 steps), the processor 120 may determine that the initial condition is not satisfied, and may not include the data in a workout 2 750. For example, since the objects (for example 767 and 768) do not generate steps per minute and do not satisfy the initial condition to be included in the cluster, the objects 767 and 768 may not be included in the workout 2 750. The processor 120 may include, in the cluster 2 760, a case where the number of steps per minute is equal to or greater than a predetermined number of steps (e.g., 10 steps), or where the average number of steps for 10 minutes is equal to or greater than a predetermined number of steps (e.g., average 100 steps). When the objects (for example, 761 and 762), which have generated the average 100 steps or more for 10 minutes, are included in the cluster 2 760, the processor 120 may also include the objects (for example 763, 764, and 765), which have generated 10 steps or more per one minute, in the cluster 2 760. The processor 120 may determine that an object 766 walking less than 10 steps corresponds to a termination condition. The processor 120 may do not include the object 766 walking less than 10 steps in the cluster 2 760.

Figure 8:
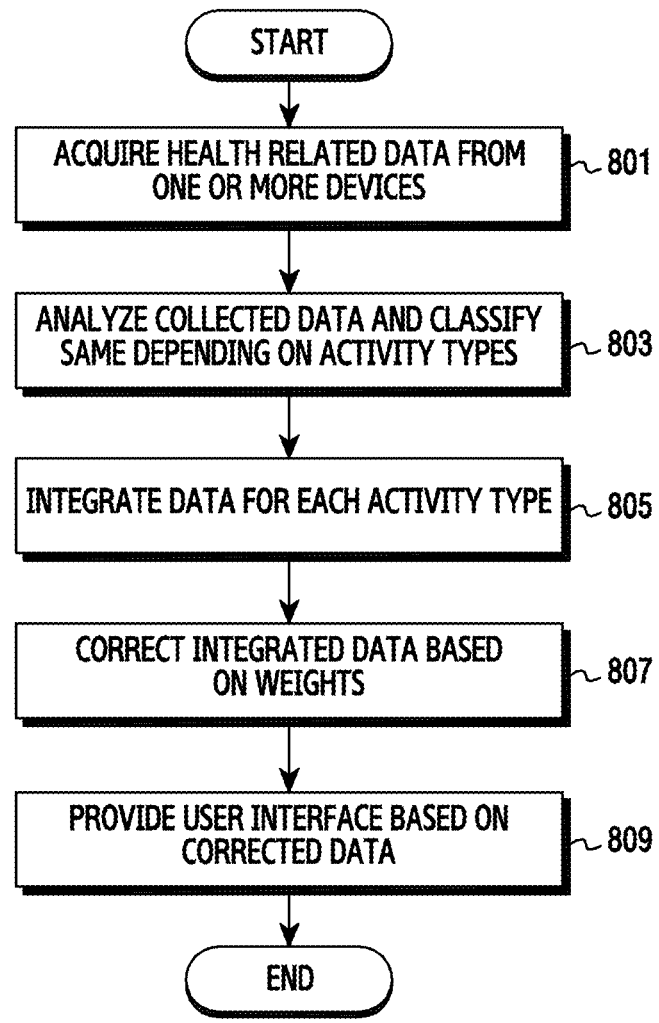
FIG. 8 illustrates a data integration method by an electronic device according to various embodiments.

FIG. 8 illustrates a data integration method of an electronic device according to various embodiments.

FIG. 8 illustrates an operation of extracting activity information using one or more pieces of data. Referring to FIG. 8, in operation 801, the electronic device 101 (e.g., the processor 120) may collect health related data from one or more devices. The processor 120 may receive health related data from the external device (or external electronic device) (e.g., one of the electronic device 102, the electronic device 104, and the wearable device 1 420 to the wearable device 450) through the communication interface 170. Alternatively, the electronic device 101 may acquire health related data using various sensor modules (e.g., the sensor module 240 of FIG. 2).

According to various embodiments, the electronic device 101 may include a first wireless sensor in the housing (or body). The housing may be analyzed as a frame (or case) that receives components of the electronic device 101 (e.g., the processor 120, the memory 130, etc.). The first wireless sensor may be a sensor (e.g., the sensor module 240) that measures the number of steps, activity information, and non-activity information. The processor 120 may monitor the movement of the housing using the first wireless sensor so as to generate first data for a first time period. In addition, the external device may include a second wireless sensor. The second wireless sensor may be a sensor (e.g., the step number counting unit 421 and workout measurement unit 422) that measures the number of steps, activity information, and non-activity information of the external device. The processor 120 may generate a wireless communication channel (e.g., a communication protocol associated with the external device) with the external device using the communication interface 170 (or referred to as a "wireless communication circuit"). The processor 120 may receive the second data acquired for the first time period through the wireless communication channel, and calculate, as a value for the first time period, a value smaller than the sum of a first value based on the first data and a second value based on the second data.

In operation 803, the electronic device 101 (for example, the processor 120) may analyze the collected data and classify the same depending on activity types. For example, the processor 120 may correct the data as shown in operation 603 of FIG. 6 before the data analysis is performed. Since the unit time for storing data is different for each device, a pre-processing operation is required to process data received from a plurality of devices. The processor 120 may divide the received data according to a unit time (e.g., one minute) for storing data of the electronic device 101. The processor 120 may analyze the corrected data and classify the corrected data depending on the activity types. For example, the activity types may be classified into three categories of the number of steps (e.g., first activity type), activity information (e.g., second activity type), and non-activity information (e.g., third activity type). Hereinafter, three classifications of activity types are described as examples, but the activity types are not limited to thereto.

According to various embodiments, the classifications of data depending on the activity types may be for easily integrating data with different characteristics. For example, the processor 120 may classify the number of steps, activity information, and non-activity information for each device.

For example, the number of steps may have the characteristics of being constantly taken by a user, and the start and the end may not be clear. This is because, if movement is detected even during sleeping or sitting, it may be determined that a number of steps has been taken by a user. In addition, due to various issues such as hardware constraints and data accuracy of external devices, the unit time for storage are very diverse, such as 1 day, 10 minutes, 5 minutes, and the like. Therefore, in order to provide more accurate and meaningful number of steps to the user, it may be required to correct the number of steps detected by each of the plurality of external devices.

The activity information may be the record of activities having a clear start and end such as running, walking, swimming, cycling, yoga, and the like. Such activity information may be automatically recognized and stored by a user or an external device or the electronic device 101. However, the activity information may be detected in duplicate when collected from a plurality of devices.

The non-activity information may be a record that represents a state where a user is in a state of being inactive, such as sleeping, resting (e.g., sitting), and the like. Such non-activity information may cause an empty space in which there is no detection because a recognition rate differs for each device. When such empty spaces are integrated, some erroneous recognition of activities, that is, a case where a sleeping state or a sitting situation that is falsely recognized as walking may be excluded, more accurate information may be provided to the user.

In operation 805, the electronic device 101 (for example, the processor 120) may integrate data for each activity type. For example, the processor 120 may list the number of steps, activity information, or non-activity information in a time sequence, and may integrate data of the same activity type into one piece of data. According to various embodiments, the processor 120 may integrate the data based on the priority of at least one of time, an activity type, a workout type, and a device. The priority may be configured by the user or configured to the electronic device 101 by a default value. For example, the processor 120 may integrate data based on the activity type occurred the very first time when the time has a higher priority. Alternatively, when the activity type has a higher priority, the processor 120 may integrate the data based on the start and end of at least one of the number of steps, the activity information, or the non-activity information, and may integrate data for the remaining activity types. For example, when the activity information has a priority, and when the activity information and the number of steps or the non-activity information overlap to each other, the processor 120 may integrate data on the activity information based on the start and end of the activity information, and integrate data on the number of steps or the non-activity information.

Alternatively, when the workout type has a higher priority, the processor 120 may integrate the data based on the start and end of at least one of walking, running, cycling, swimming, and may integrate the data for the remaining activity types. For example, when the cycling has a higher priority, the processor 120 may integrate data for cycling based on the start and end of cycling, and integrate data on the remaining activity information, number of steps, or non-activity information. Alternatively, when the device has a higher priority, the processor 120 may integrate at least one of number of steps, activity information, or non-activity information of a device having a lower priority, based on the start and end of a device having a higher priority.

A method for integrating data for the number of steps, the activity information, and the non-activity information will be described in detail with reference to the following drawings.

In operation 807, the electronic device 101 (for example, the processor 120) may correct the integrated data based on weights. According to various embodiments, the processor 120 may assign different weights to at least one of an activity type, a workout type, and a device. For example, when a weight is assigned to an activity type, since it may be determined that the activity information is more meaningful to a user than the number of steps or the non-activity information, the processor 120 may assign a higher weight to the activity information. For example, when performing data correction, the processor 120 may configure higher weights in the sequence of activity information, non-activity information, and number of steps. Since the number of steps is always automatically counted and the error recognition rate is high due to technical limitations, it may be configured to assign the lowest weight to the number of steps. Alternatively, with respect to assigning weights to workout types, more accurate activity information may be provided to the user by assigning a higher weight to cycling, swimming, etc., which have more clear start and end times than walking or running has. Alternatively, with respect to assigning weights to the device, more accurate activity information may be provided to the user by assigning a higher weight to the electronic device 101 than the external device.

According to various embodiments, the processor 120 may assign different weights to at least one of an activity type, a workout type, and a device, respectively, and may correct data by comprehensively considering each weight. For example, the processor 120 may configure different weights on workout types or devices depending on activity types. When the second activity type on the activity information has a higher weight, the processor 120 may assign a higher weight to the external device than the electronic device 101. Alternatively, the processor 120 may configure a different weight for each device according to the workout type. When the workout type is swimming, the processor 120 may assign a higher weight to the external device than the electronic device 101, and when the workout type is cycling, the processor 120 may assign a higher weight to the electronic device 101 than the external device. This method may be intended to provide more meaningful and more accurate information to the user.

According to various embodiments, the processor 120 may integrate data based on the priorities, but may also correct the integrated data based on the weights. That is, when integrating data according to the priority in operation 805, the processor 120 may skip the operation 807 without performing thereof. Alternatively, when integrating data according to the priority in operation 805, the processor 120 may perform the operation 807. According to various embodiments, the weight may be configured by the user or configured to the electronic device 101 by a default value. According to various embodiments, the processor 120 may assign a different weight to each priority, and may correct data by comprehensively considering each weight. For example, the weight configured to perform the data correction may be proportional or inversely proportional to the priority configured to perform the data integration. For example, when the priority configured to perform the data integration is high, the weight configured to perform the data correction may also be high. Alternatively, when the priority configured to perform the data integration is high, the weight configured to perform the data correction may be low.

In operation 807, the electronic device 101 (for example, the processor 120) may provide a user interface based on the corrected data. The user interface may provide activity information on the corrected data along with activity information for each device.

According to various embodiments, the processor 120 may generate first data (e.g., number of steps, cycling, swimming, non-activity, etc.) for the first time period by using a motion sensor (e.g., sensor module 240) provided in the electronic device 101, determine a first attribute (e.g., the number of steps) of the movement of the electronic device 101 during a first session of a first time period using a first portion of the first data, determine a second attribute (e.g., activity information) of the movement of the electronic device 101 during a second session of the first time period by using a second portion of the first data, select one of the first attribute or the second attribute, and display at least one of the image, text, or symbol representing the selected attribute through a user interface displayed on the display 160.

When a user interface receives an input of a health related application selected by a user, in order to view health related data, the processor 120 may provide the user interface through the selected application. Alternatively, when each device is connected (or paired) with the electronic device 101, the processor 120 may execute an application associated with the connected device to provide the user interface. The processor 120 may attach a tag (e.g., an auto tag) to the activity information on the corrected data so as to allow a user to easily recognize the corrected data. Various embodiments for the user interface will be described in detail with reference to the following drawings.

Figure 9:
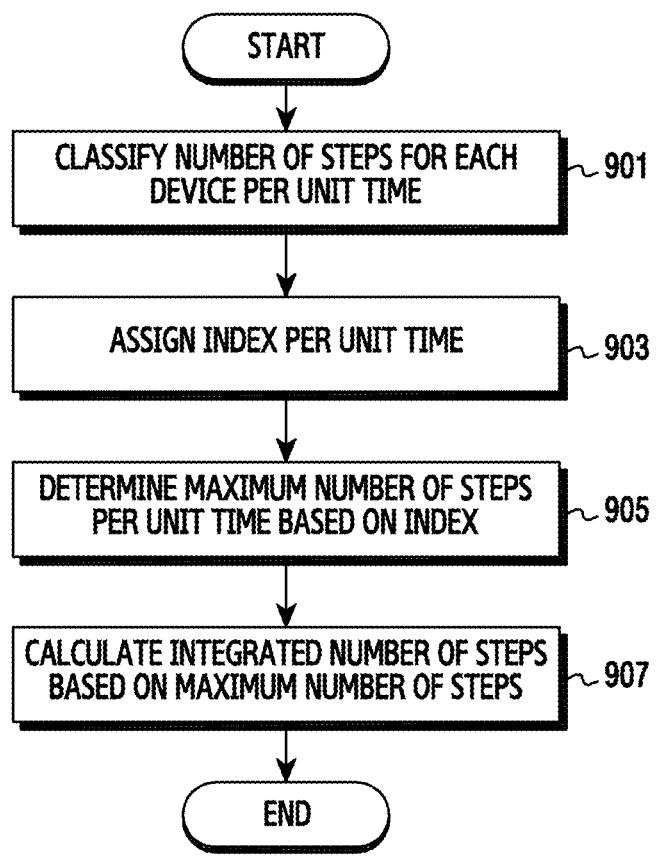
FIG. 9 illustrates a method for integrating the number of steps by an electronic device according to various embodiments.

FIG. 9 illustrates a method for integrating the number of steps by an electronic device according to various embodiments.

FIG. 9 may be a drawing that embodies the data integration operation 805 of FIG. 8. That is, FIG. 9 illustrates the operation of integrating the number of steps for the first activity type. Referring to FIG. 9, in operation 901, the electronic device 101 (e.g., the processor 120) may classify the number of steps for each device per unit time. Each device may have a different unit time for storing data according to the performance of hardware or software. For example, the number of steps may be stored in each device in various units of times, such as 1 minute, 5 minutes, 10 minutes, and the like. Thus, in order to integrate the number of steps collected from devices having different storage unit, it is required to classify data in a predetermined size. To this end, the processor 120 may classify the number of steps for each device depending on the unit time for storing data of the electronic device 101.

Although the integration of the number of steps a user has taken may be done in various methods, a method which does not allow a user to realize the reduction in the number of steps while minimizing the error may be used. For example, the Max method may be used for the method of integrating the number of steps. Since the reduction in the number of steps may be a factor that hinders a user's experience, the processor 120 may integrate the number of steps using the max method to indicate a value that is always greater than the number of steps checked in the plurality of devices. For reference, when the number of steps is integrated into the average value of a plurality of devices or other integration methods are used, the max method may be suitable because the number of steps may have the possibility of being smaller than the number of steps measured by a single device.

According to various embodiments, the processor 120 may calculate a value, as the value for a first time period, which is less than the sum of a first value based on first data autonomously generated for the first time period and a second value based on second data measured from the external device. In other words, although an embodiment of integrating the number of steps using the max method is described below, the number of steps may be integrated using other method other than the max method.

In operation 903, the electronic device 101 (for example, the processor 120) may assign an index per unit time. For example, since a day is 24 hours, a total of 1,440 indices may be assigned when the index is assigned in a unit of one minute. In mathematics, since the index is used from 0, the processor 120 may assign indices from 0 to 1339.

In operation 905, the electronic device 101 (for example, the processor 120) may determine the maximum number of steps per unit time based on the index. For example, the processor 120 may determine the maximum number of steps per unit time using Equation 1.

$source_i[x], i = step$ 1 mins binning data of source $i$ $x$ = binning index $$combined[x](source_1[x], source_2[x], \ldots source_i[x]) \quad \text{[Equation 1]}$$

The $source_i$ may refer to an external device (e.g., wearable device, electronic device 101) that has acquired the number of steps, x may refer to an index, and combined [x] may refer to the maximum number of steps per unit time. If i is 0, it may refer to the first device that has acquired the number of steps, and if i is 1, it may refer to the second device that has acquired the number of steps, and if i is i, it may refer to the i-th device that has acquired the number of steps.

Referring to Equation 1, the processor 120 may determine the number of steps as the number of steps corresponding to a unit time, which is obtained by measuring the maximum number of steps in the unit time among the number of steps measured by each of the plurality of devices.

In operation 907, the electronic device 101 (for example, the processor 120) may calculate the integrated number of steps based on the maximum number of steps. For example, the processor 120 may calculate the number of steps that is obtained by summing all the maximum number of steps per unit time, as the integrated number of steps during the time when the maximum number of steps is determined. For example, the processor 120 may integrate the number of steps measured by the wearable device 1 420 and the number of steps measured by the wearable device 3 440. Alternatively, the processor 120 may integrate the number of steps measured by the wearable device 1 420, the number of steps measured by the electronic device 101 itself, and the number of steps measured by the application installed in the electronic device 101.

Figure 10:
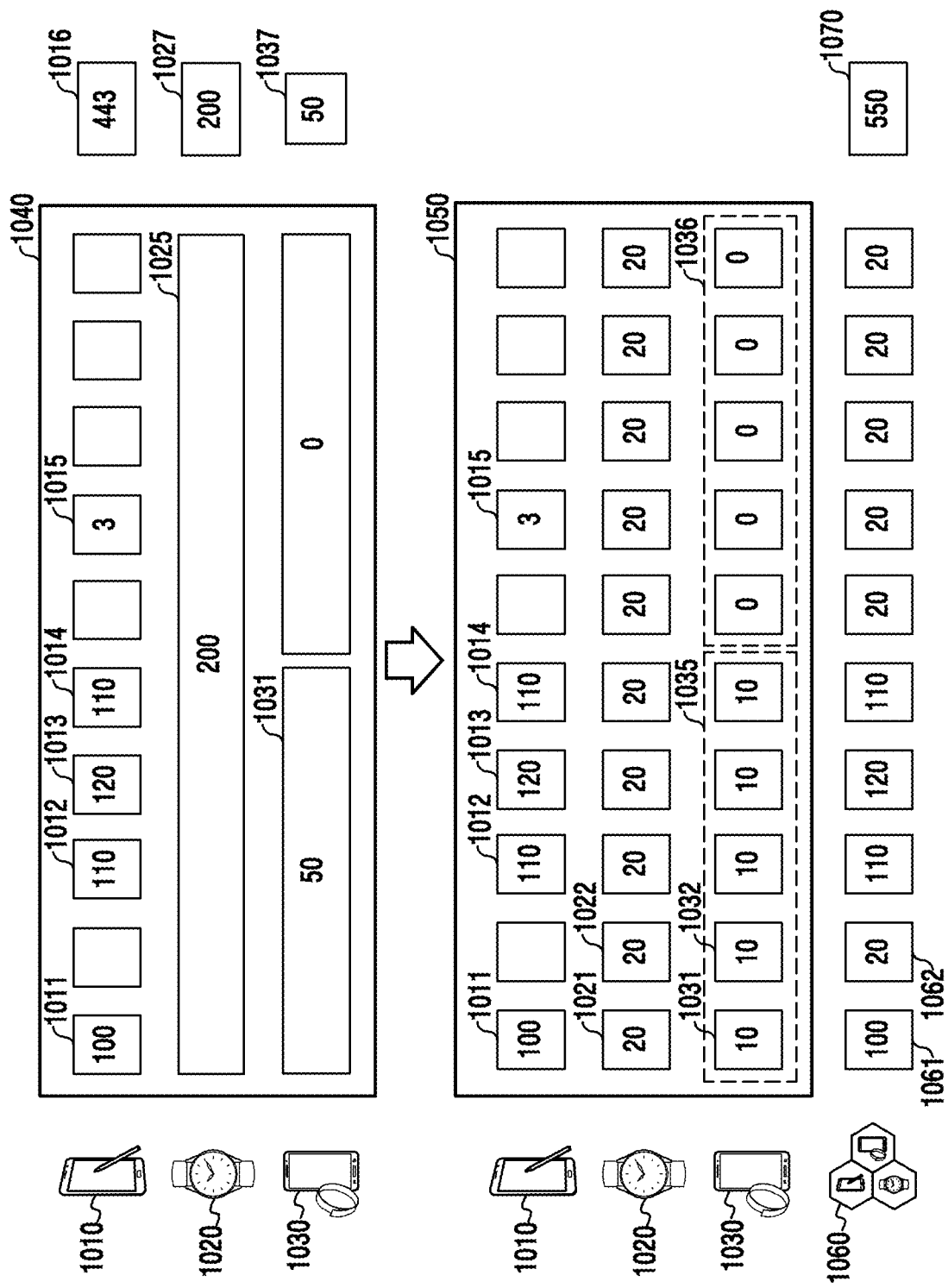
FIG. 10 illustrates an example of integrating the number of steps according to various embodiments.

FIG. 10 illustrates an example of integrating the number of steps according to various embodiments.

Referring to FIG. 10, reference numeral '1040' represents the number of steps measured by each device for a predetermined period of time (e.g., 09:00 to 09:10). The electronic device 1010 may store the number of steps in a unit of one minute, so as to acquire a total number of 443 steps 1016 for ten minutes. Since the electronic device 1010 stores the number of steps in a unit of one minute, the processor 120 may acquire, as the number of steps, 100 steps 1011 at 09:01, zero at 09:02, 110 steps 1012 at 09:03, 120 steps 1013 at 09:04, 110 steps 1014 at 09:05, zero at 09:06, 3 steps 1015 at 09:07, and zero from 09:08 to 09:10. The wearable device 1020 may store the number of steps in a unit of ten minutes, so as to acquire a total of 200 steps 1027 for ten minutes. For example, the wearable device 1020 may store the number of steps in units of 10 minutes, the wearable device 1020 may acquire, as the number of steps, 200 steps 1025 from 09:00 to 09:10. The application 1030 installed in the electronic device 1010 may store the number of steps in a unit of 5 minutes, and acquire a total of 50 steps 1037 for 10 minutes. Since the application 1030 stores the number of steps in a unit of 5 minutes, the application 1030 may acquire, as the number of steps, 50 steps 1031 from 09:00 to 09:05, and zero from 09:06 to 09:10.

According to various embodiments, when the number of steps is divided in a unit of one minute by the wearable device 1020 or the application 1030, the processor 120 may not accurately know the time point of the occurrence of the number of steps so that the total number of steps may be divided by 10 to become an average value.

Reference numeral '1050' indicates the classification of the number of steps measured by each device in a unit of one minute for a predetermined time (e.g., from 09:00 to 09:10). Since the wearable device 1020 stores the number of steps in a unit of 10 minutes, the number of steps in a unit of one minute may be calculated by dividing the total number of steps 1027 by 10 in order to divide in a unit of one minute. The number of steps in a unit of one minute of the wearable device 1020 may be 20 steps 1021. That is, the processor 120 may acquire the number of steps in a unit of one minute of the wearable device 1020, as 20 steps 1021 at 09:01, 20 steps 1022 at 09:02, and 20 steps from 09:03 to 09:10, respectively. Since the application 1060 stores the number of steps in a unit of five minutes, the number of steps in a unit of one minute may be calculated by dividing 50 steps 1031 by five, which is the number of steps in units of five minutes (e.g., from 09:00 to 09:05), and dividing 0 steps by five, which is the remaining number of steps in a unit of five minutes (e.g., from 09:06 to 09:10) in order to divide in a unit of one minute. The number of steps in a unit of one minute of the application 1060 may be 10 steps 1035 from 09:00 to 09:05, and may be zero 1036 from 09:06 to 09:10. In other words, the processor 120 may acquire 10 steps 1035 from 09:00 to 09:05, and zero 1036 from 09:06 to 09:10, so as to acquire the number of steps of the application 1030 in a unit of one minute.

The processor 120 may determine the maximum number of steps among the number of steps per unit time as the number of steps per unit time. The processor 120 may perform the integration 1060 of the number of steps of a plurality of devices by applying Equation 1. For example, since, at 09:01, the number of steps of the electronic device 1010 is 100 steps 1011, the number of steps of the wearable device 1020 is 20 steps 1021, and the number of steps of the application 1030 is 10 steps 1035, and therefore, the maximum number of steps may be 100 steps 1011, which is the number of steps of the electronic device 1010. In this case, the processor 120 may determine the number of steps at a unit time of 09:01 as 100 steps 1061, which is the maximum number of steps.

Similarly, since, at 09:02, the number of steps of the electronic device 1010 is zero, the number of steps of the wearable device 1020 is 20 steps 1022, and the number of steps of the application 1030 is 10 steps 1032, the maximum number of steps may be 20 steps 1022, which is the number of steps of the wearable device 1020. In this case, the processor 120 may determine the number of steps at a unit time of 09:02 as 20 steps 1062, which is the maximum number of steps. The processor 120 may calculate the maximum number of steps during 09:03 to 09:10 as described above, and calculate the integrated number of steps, as 550 steps 1070, which has summed all the calculated maximum number of steps. It can be seen that 550 steps 1070, which is the integrated number of steps, is greater than the integrated number of steps (e.g., 1016, 1027, and 1037) measured by the individual sources. When the number of steps is integrated using the max method, the user experience related to the reduction of the number of steps may be reduced.

According to various embodiments, the processor 120 may calculate, as a value (e.g., the integrated number of steps) for a first time period, a value (e.g., 550 steps 1070) which is smaller than the sum of a first value (e.g., 443 steps 1016) based on the first data (e.g., the number of steps measured by the electronic device 1010) acquired for the first time period (e.g., from 09:00 to 09:10) and a second value (e.g., 200 steps 1027) based on the second data (e.g., the number of steps measured by the wearable device 1020).

Figure 11:
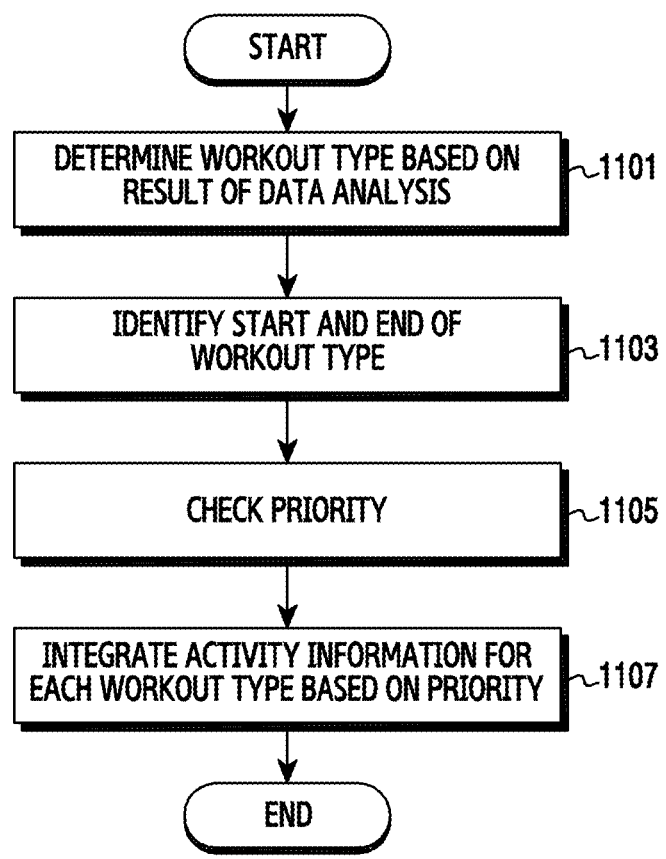
FIG. 11 illustrates a method for integrating activity information by an electronic device according to various embodiments.

FIG. 11 illustrates a method for integrating activity information by an electronic device according to various embodiments.

FIG. 11 may be a drawing that embodies the data integration operation 805 of FIG. 8. That is, FIG. 11 illustrates the operation of integrating the activity information on the second activity type. Referring to FIG. 11, in operation 1101, the electronic device 101 (e.g., the processor 120) may determine a workout type based on the result of data analysis. The workout type may be obtained by classifying various workouts, such as walking, running, cycling, swimming, yoga, and the like. According to various embodiments, the processor 120 may determine, on the basis of the result of data analysis, that the workout type is 'running' when the number of steps measured for one minute is equal to or greater than the first predetermined number of steps (e.g., 150 steps), and determine that the workout type is 'walking' when the number of steps measured for one minute is less than the first predetermined number of steps. The processor 120 may compare the determined sum of the walking with the sum of the running, and determine a workout, which has a larger value, as the workout type. For example, if the sum of the walking is 1000 and the sum of the running is 400, the processor 120 may determine the type of workout as 'walking'. The first predetermined number of steps may be configured by the user or configured to the electronic device 101 by default.

According to various embodiments, the processor 120 may calculate a movement speed based on a change in location information for 10 minutes when the number of steps taken during a predetermined period of time is equal to or greater than the second predetermined number of steps (e.g., 1000 steps). When the calculated moving speed is equal to or higher than a predetermined speed (e.g., 20 Km/h), the processor 120 may identify that the moving speed corresponds to cycling, and determine the workout type as 'cycling'. In addition, when the calculated moving speed is less than a predetermined speed (e.g., 20 Km/h), the processor 120 may identify that the moving speed corresponds to running, and determine the workout type as 'running'. The predetermined speed may be configured by the user or configured to the electronic device 101 by default.

In operation 1103, the electronic device 101 (for example, the processor 120) may identify the start and end of the workout type. The processor 120 determines a workout type using data detected from a plurality of devices, but the start time and end time of the workout type may be different for each device. The processor 120 may check the start time and the end time of the workout type measured by each device. For example, the start time of the cycling, measured by the wearable device 1020, is 09:30, and the start time autonomously measured by the electronic device 101 may be 09:20. Alternatively, the end time of the cycling, measured by the wearable device 1020, is 10:30, and the end time autonomously measured by the electronic device 101 may be 10:20. In this case, since the start time and the end time are different for one workout type, it is required to match the start time and the end time for the data integration. In operation 1105, the electronic device 101 may check the priority. The priority may be at least one of time, an activity type, a workout type, and a device. The priority may be configured by the user or configured to the electronic device 101 by a default value, and then stored in the memory 130. The processor 120 may check whether the priority associated with the activity information is stored in the memory 130.

In operation 1107, the electronic device 101 (for example, the processor 120) may integrate activity information for each workout type based on the priority. For example, when giving a higher priority to time, the processor 120 may integrate activity information based on the start time and the end time of the workout type that has occurred for the very first time. Alternatively, when giving a higher priority to the workout type, the processor 120 may integrate activity information based on the start time and the end time of the workout type that has a higher priority. For example, when the priority is higher in the sequence of cycling, walking, running, and swimming, and the workout times of cycling and walking are partially overlapped, the processor 120 may integrate the activity information of the cycling based on the start time and the end time of cycling. The processor 120 may determine the workout time of walking so as not to overlap with the workout time of cycling, and integrate activity information of the walking.

When the priority is given to the device, the priority is higher in the sequence of the external device, the electronic device 101, and an application. For example, the processor 120 may integrate the activity information based on the workout time of the workout type measured by the external device, and integrate the activity information using the workout time of the workout type measured by the electronic device 101.

Figure 12:
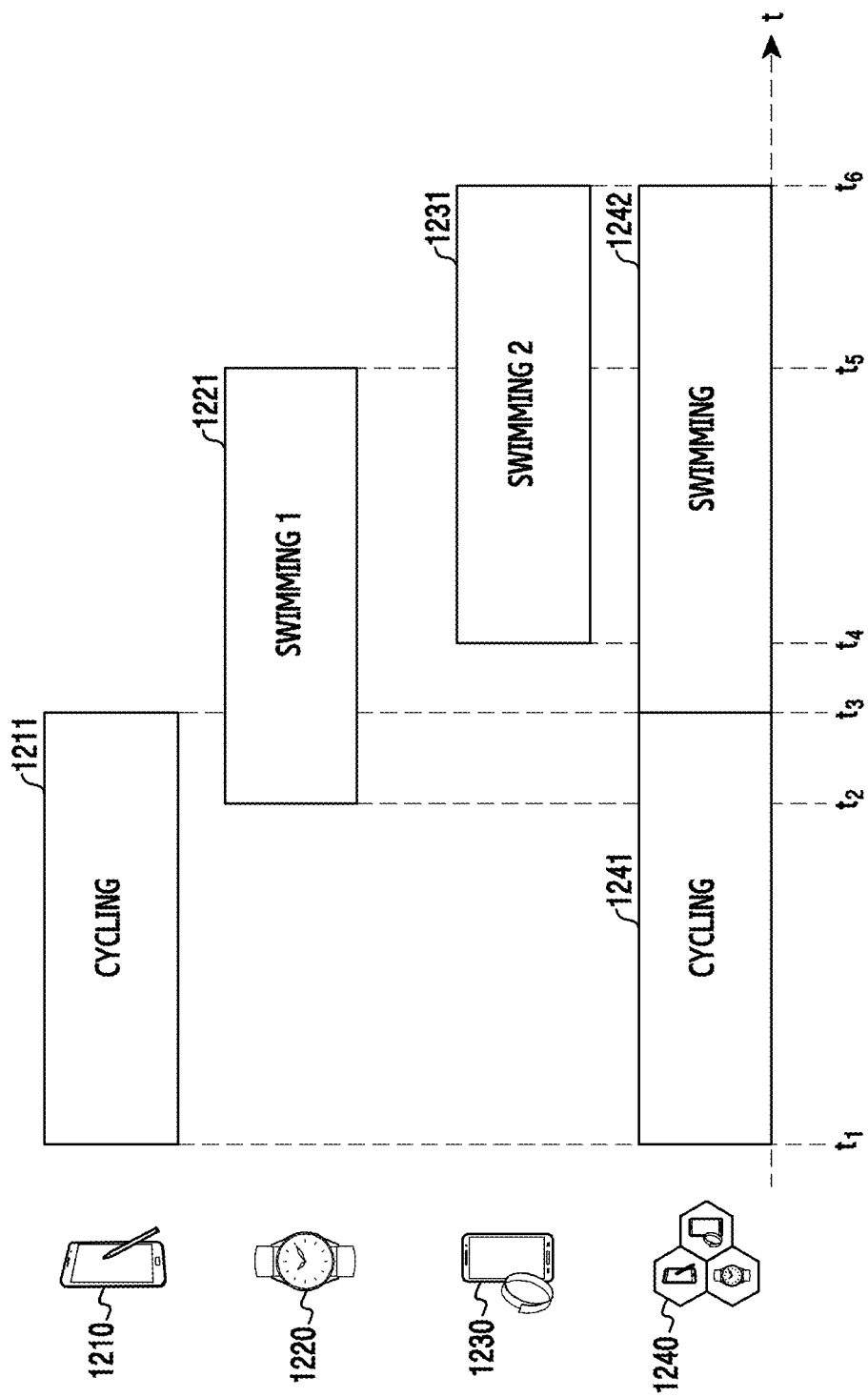
FIG. 12 illustrates an example of integrating activity information according to various embodiments.

FIG. 12 illustrates an example of integrating activity information according to various embodiments.

Referring to FIG. 12, the processor 120 may integrate activity information based on the start time of the workout type. For example, when it is recognized that the cycling 1211 has started first, as a result of analysis of the data measured by the application 1210, the processor 120 may integrate the activity information 1241 on the cycling based on the start time t1 of the cycling 1211. The application 1210 may refer to an application installed in the electronic device 1220. The processor 120 may check the end time t3 of the cycling 1211 and determine whether the end time t3 of the cycling 1211 overlaps with other activity information.

Since the processor 120 integrates the activity information based on time, when the activity information (e.g., first activity information) that has started first overlaps other activity information (e.g., second activity information), the processor 120 may integrate the second activity information based on the end time of the first activity information. For example, it can be seen that the end time t3 of the cycling 1211 overlaps the start time t2 of the swimming 1 1221 measured by the electronic device 1220. In this case, the processor 120 may integrate the activity information 1241 on the cycling until the end time t3 of the cycling 1211, and integrate the activity information on the swimming after the end time t3 of the cycling 1211.

For example, a user may swim after configuring the swimming start time on the electronic device 1220 before beginning swimming. Alternatively, a user may configure an expected swimming time (e.g., 30 minutes, one hour, etc.) to the electronic device 1220. In this case, the swimming time actually taken by a user may be different from the swimming workout time measured by the electronic device 1220. However, a user may swim by attaching the electronic device 1220 to the body, and in general the user may swim by wearing the wearable device 1230. For example, the start time t2 of the swimming 1 1221 measured by the electronic device 1220 may be different from the time t4 measured for the swimming 2 1231 measured by the wearable device 1230. In addition, the end time t5 of the swimming 1 1221 measured by the electronic device 1220 may be different from the end time t6 measured for the swimming 2 1231 measured by the wearable device 1230.

In consideration of the above description, when integrating activity information on the swimming, the processor 120 may integrate the activity information 1242 on the swimming based on data on the swimming 1 1221 measured by the electronic device 1220 and data on the swimming 2 1231 measured by the wearable device 1230. The processor 120 may integrate the activity information 1242 on the swimming based on the workout time t2 to t5 of the swimming 1 1221, measured by the electronic device 1220, after the end time t3 of the cycling 1211, and the workout time t4 to t6 of the swimming 2 1231 measured by the wearable device 1230. In this case, activity information acquired from different devices is processed as one continuous activity, so that the user may intuitively identify the activity information.

According to various embodiments, when integrating activity information, the activity information may be integrated by assigning different priorities to each device. Unlike cycling, it can be seen that two devices have measured the swimming. The processor 120 may assign different priorities to each device, so as to integrate the activity information. For example, in FIG. 12, the wearable device 1230 may have a higher priority than the electronic device 1220. The processor 120 may assign a higher priority to the workout time t4 to t6 of the swimming 2 1231 measured by the wearable device 1230 than the workout time t2 to t5 of the swimming 1 1221 measured by the electronic device 1220, so as to integrate the activity information 1242 on the swimming.

Figure 13:
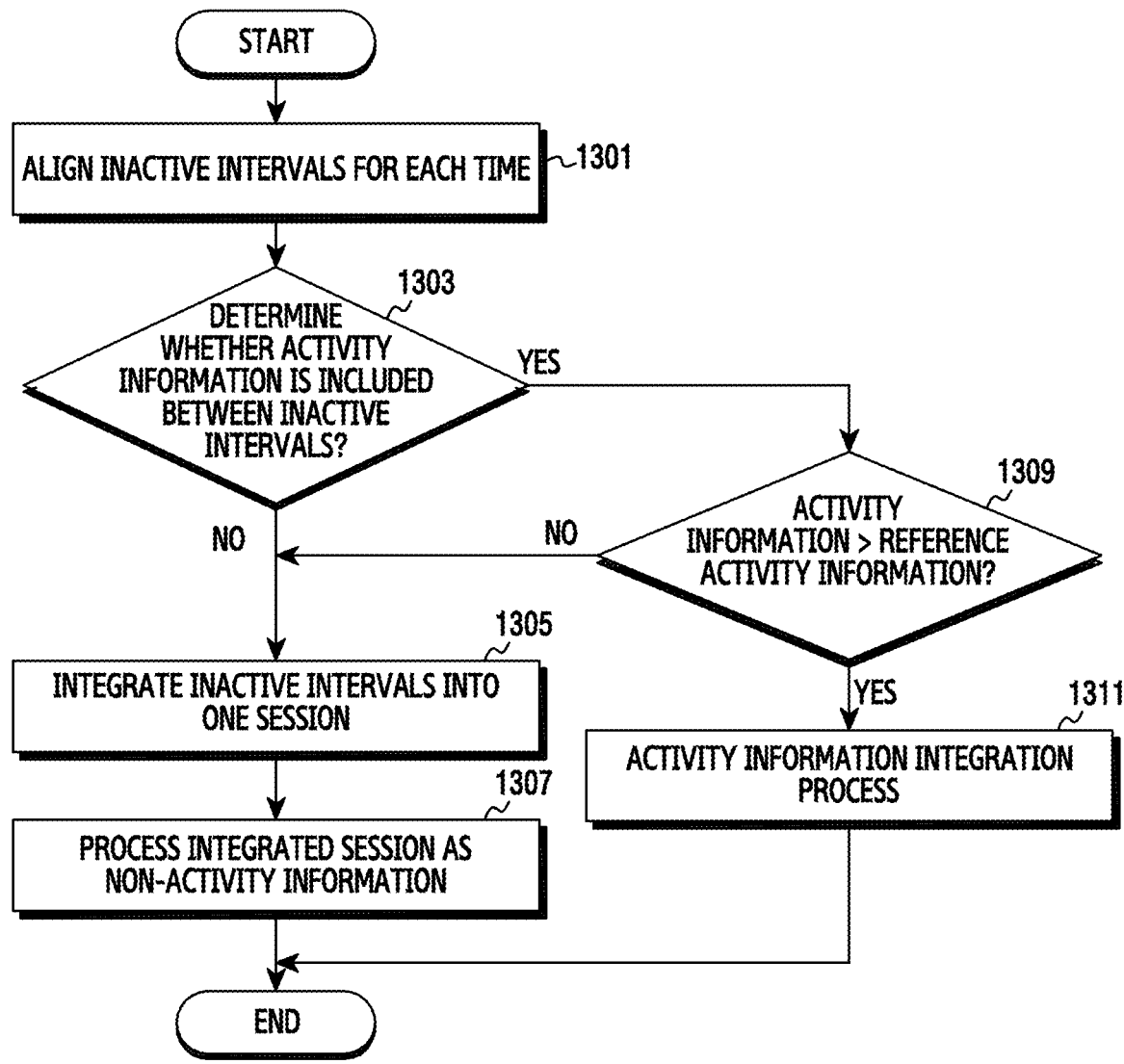
FIG. 13 illustrates a method for integrating non-activity information by an electronic device according to various embodiments.
Figure 14:
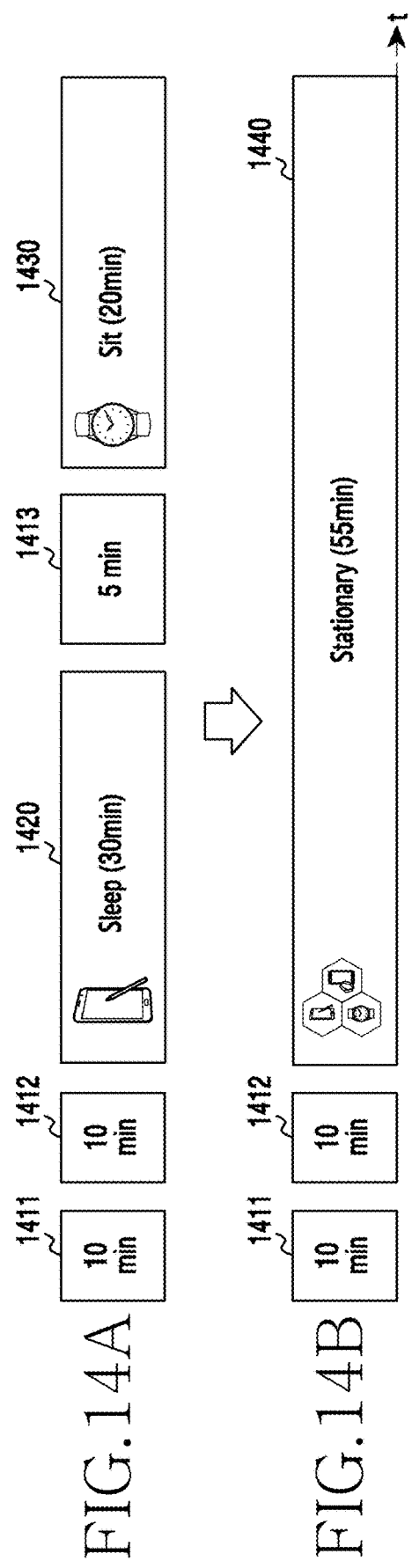
FIGS. 14A and 14B illustrate an example of integrating non-activity information according to various embodiments.

FIG. 13 illustrates a method for integrating non-activity information by an electronic device according to various embodiments.

FIG. 13 may be a drawing that embodies the data integration operation 805 of FIG. 8. That is, FIG. 13 illustrates the operation of integrating non-activity information on a third activity type. Referring to FIG. 13, in operation 1301, the electronic device 101 (e.g., the processor 120) may align inactive intervals for each time. The inactive intervals may mean a stationary state such as taking a sleep, sitting, and the like without walking or activity (e.g., cycling, swimming, etc.). Alternatively, the inactive intervals may mean that there is no detection. The processor 120 may align the inactive intervals for each time.

In operation 1303, the electronic device 101 (e.g., processor 120) may determine whether activity information is included between inactive intervals. For example, the number of steps may be taken by a walker during a break. In this case, since the number of steps has been taken by a user when moving, such as going to the restroom in the middle of rest, and the like, the activity information may be included between inactive intervals.

When the activity information is included between the inactive intervals, the operation 1309 may be performed, and when the activity information is not included therebeween, an operation 1305 may be performed.

In operation 1305, the electronic device 101 (for example, the processor 120) may integrate the inactive intervals into one session. The inactive interval may be integrated through a distance based clustering. For example, when the inactive interval is continuously displayed, the processor 120 may integrate the inactive intervals that have been continuously detected into one session.

In operation 1307, the electronic device 101 (for example, the processor 120) may process the integrated session as non-activity information. The processor 120 may store the processed non-activity information in the memory 130.

In operation 1309, the electronic device 101 (e.g., processor 120) may determine whether activity information included between inactive intervals exceeds the reference activity information. The reference activity information may be configured by the user or configured to the electronic device 101 by a default value, and then stored in the memory 130. When the inactive interval is continuously displayed, it is highly likely that activity information for a very short time period recognized in the middle may be wrongly recognized. Accordingly, the reference activity information may be used for processing a small movement between inactive intervals as an error, for example, the reference activity information may be 10 steps or less, 5 minutes or less, and so on. The processor 120 may return to the operation 1305 when the activity information included between the inactive intervals is less than or equal to the reference activity information.

When the activity information included between the inactive intervals exceeds the reference activity information, the processor 120 may perform an operation 1311, and when the activity information included between the inactive intervals is less than or equal to the reference activity information, the processor 120 may perform the operation 1305.

In operation 1311, the electronic device 101 (e.g., processor 120) may perform an activity information integration process when the activity information included between inactive intervals exceeds the reference activity information. The activity information integration process may be an operation described in FIG. 11.

FIGS. 14A and 14B illustrate an example of integrating non-activity information according to various embodiments.

Referring to FIGS. 14A and 14B, as shown in FIG. 14A, the inactive intervals may be aligned in a time sequence. When there is no data detection, the processor 120 may process the case as an 'unknown interval' such as an object 1411 and an object 1412. The unknown interval may refer to an interval in which there is no data detection in an external device, the electronic device 101, or an application, which measure health related data. The processor 120 may analyze data collected in one or more devices, and when there is no measured data, as a result of analysis, the processor 120 may process the case as an 'unknown interval'. The processor 120 may analyze the data measured by the electronic device 101 as sleep 1420. In addition, the processor 120 may analyze the data measured by the external device as sitting 1430. The processor 120 may recognize the sleep 1420 measured by the electronic device 101 as an inactive interval (e.g., first inactive interval), and recognize the sitting 1430 measured by the external device as an inactive interval (e.g., second inactive interval). When there is no data detection between data measured by the electronic device 101 and the data measured by the external device, the processor 120 may process the case as an unknown interval 1413.

The processor 120 may integrate inactive intervals, as shown in FIG. 14B. For example, the processor 120 may determine an unknown interval 1413 between the first inactive interval (e.g., sleep 1420) and the second inactive interval (e.g., sitting 1430) as continuous inactive intervals. The processor 120 may use the minimum distance by 10 minutes and determine total 55 minutes as inactivity information. The processor 120 may integrate the interval from a first inactive interval (e.g., sleep 1420) to a second inactive interval (e.g., sitting 1430) into one session. The processor 120 may process an integrated session that includes a first inactive interval (e.g., sleep 1420), an unknown interval 1413, a second inactive interval (e.g., sitting 1430) as inactivity information (stationary) 1440.

Figure 15:
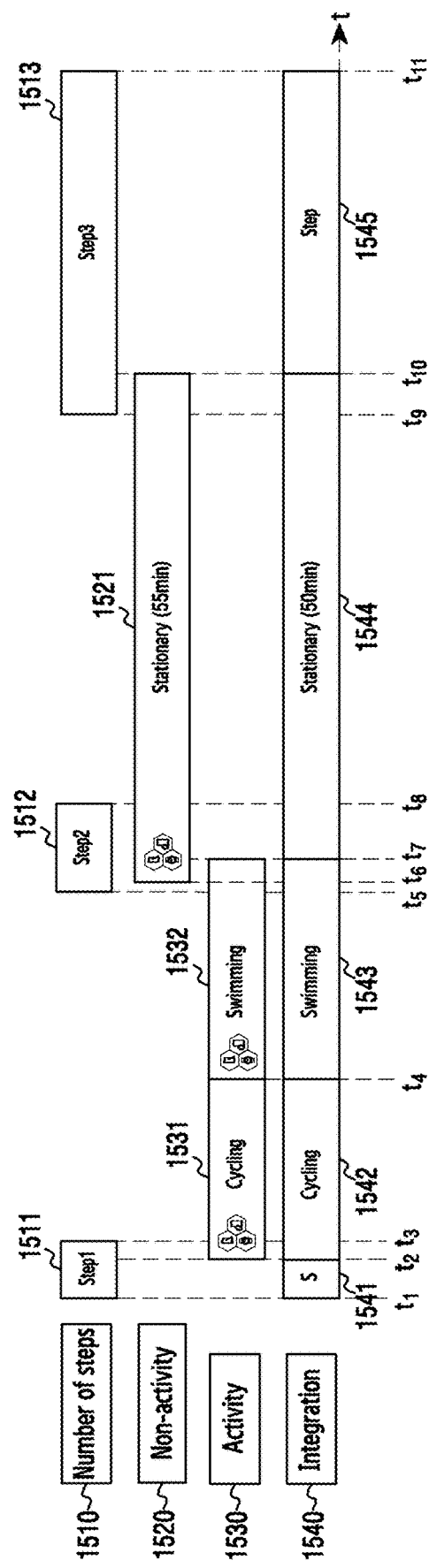
FIG. 15 illustrates an example of integrating data of various activity type according to various embodiments.

FIG. 15 illustrates an example of integrating various activity type data according to various embodiments.

Referring to FIG. 15, the processor 120 may integrate number of steps 1510, inactivity information 1520, and activity information 1530 according to each activity type, as shown in FIG. 9 to FIG. 14B (indicated by reference numeral 1540), and correct the integrated data by considering the priority (or weight) of the activity type. Alternatively, the processor 120 may integrate the number of steps 1510, inactivity information 1520, and activity information 1530 by considering the priority (or weight) of the activity type.

The processor 120 may integrate the number of steps 1 (Step 1, 1511) from t1 to t3 (e.g., 9 minutes), integrate the number of steps 2 (Step 2, 1512) from t5 to t8 (e.g., 9 minutes), and integrate the number of steps 3 (Step 3, 1513) from t9 to t11 (e.g., 30 minutes). In addition, the processor 120 may integrate inactivity information 1521 from t6 to t10. In addition, the processor 120 may integrate activity information on the cycling 1531 from t2 to t4, and integrate activity information on the swimming 1532 from t4 to t7.

According to various embodiments, the priority may be higher in the order of the activity information 1530, the inactivity information 1520, and the number of steps 1510. The processor 120 may configure a higher priority to the activity information 1530 because it may be determined that the activity information 1530 is more meaningful to a user than the number of steps 1510 or the inactivity information 1520. For reference, since the number of steps 1510 has a high error recognition rate, the processor 120 may configure the lowest priority to the number of steps 1510.

According to various embodiments, since the priority of the activity information 1530 is higher than the number of steps 1510 when the activity information for the number of steps 1 1511 overlaps the activity information for the cycling 1531, the processor 120 may correct the number of steps 1 1511 based on the activity information on the cycling 1531. For example, when the start time t2 of the cycling 1531 between the start time t1 and the end time t3 of the number of steps 1 1511 overlap with each other, the processor 120 may correct the end time t3 of the number of steps 1 1511 to be the start time t2 of the cycling 1531. That is, the corrected number of steps (S) 1541 may be corrected so as to be generated during the time from t1 to t2. In addition, activity information 1542 on the cycling 1531 may be corrected so as to be generated during the time from t2 to t4.

For the same activity type (e.g., activity information 1530), the processor 120 may correct the workout time based on at least one of a time, a workout type, and a device. For example, the processor 120 may correct the activity information 1543 on the swimming 1532, after the correction of the activity information 1542 on the cycling 1531 has been completed, which has first started based on time. When the end time t7 of the swimming 1532, the start time t5 of the number of steps 2 1512, and the start time t6 of the inactive interval 1521 are overlapped to each other, the processor 120 may place a priority on the swimming 1532 based on the priority of the activity type, and correct the number of steps 2 1512 and the inactive interval 1521 after the end time t7 of the swimming 1532. Accordingly, activity information 1543 on the swimming 1532 may be corrected so as to be generated during the time from t4 to t7.

Here, since the error recognition rate of the number of steps 1510 is high, the processor 120 may correct the number of steps 2 1512 based on the start time t6 of the inactive interval 1521 when the start time t5 of the number of steps 2 1512 and the start time t6 of the inactive interval 1521 are overlapped. In this case, the number of steps 2 1512 may not be included in the integrated data. That is, when the number of steps 2 1512 is temporarily generated during the inactive interval 1521, the processor 120 may process the number of steps 2 1512 as an error.

To this end, the processor 120 may determine whether the number of steps 2 1512 that has been generated from the start time of the inactive interval 1521 exceeds the reference activity information. The reference activity information may be used for processing a small movement between inactive intervals as an error, for example, the reference activity information may be 10 steps or less, 5 minutes or less, and so on. When the number of steps 2 1512 that has been generated in the inactive interval 1521 is less than or equal to the reference activity information, the processor 120 may process the number of steps 2 1512 as an error and do not include the same in the integrated data. That is, the processor 120 may ignore the number of steps 2 1512 and do not include the same in the integrated data.

In addition, when the end time t10 of the inactive interval 1521 overlaps the start time t9 of the number of steps 3 1513, the processor 120 may correct the number of steps 3 1513 based on the end time t10 of the inactive interval 1521. In this case, the processor 120 may determine whether the number of steps 3 1513 that has been generated from the start time t9 of the number of steps 3 1513 to the end time t10 of the inactive interval 1521 exceeds the reference activity information. The processor 120 may process a part of the number of steps 3 1513 as an error when the number of steps 3 1513 that has been generated until the end time t10 of the inactive interval 1521 is less than or equal to the reference activity information. Therefore, the inactivity information 1544 may be corrected so as to be generated during the time from t7 to t10. In this case, the corrected number of steps 1545 may be corrected so as to be generated during the time from t10 to t11.

Accordingly, the processor 120 may store the corrected data 1540 to the memory 130.

Figure 16:
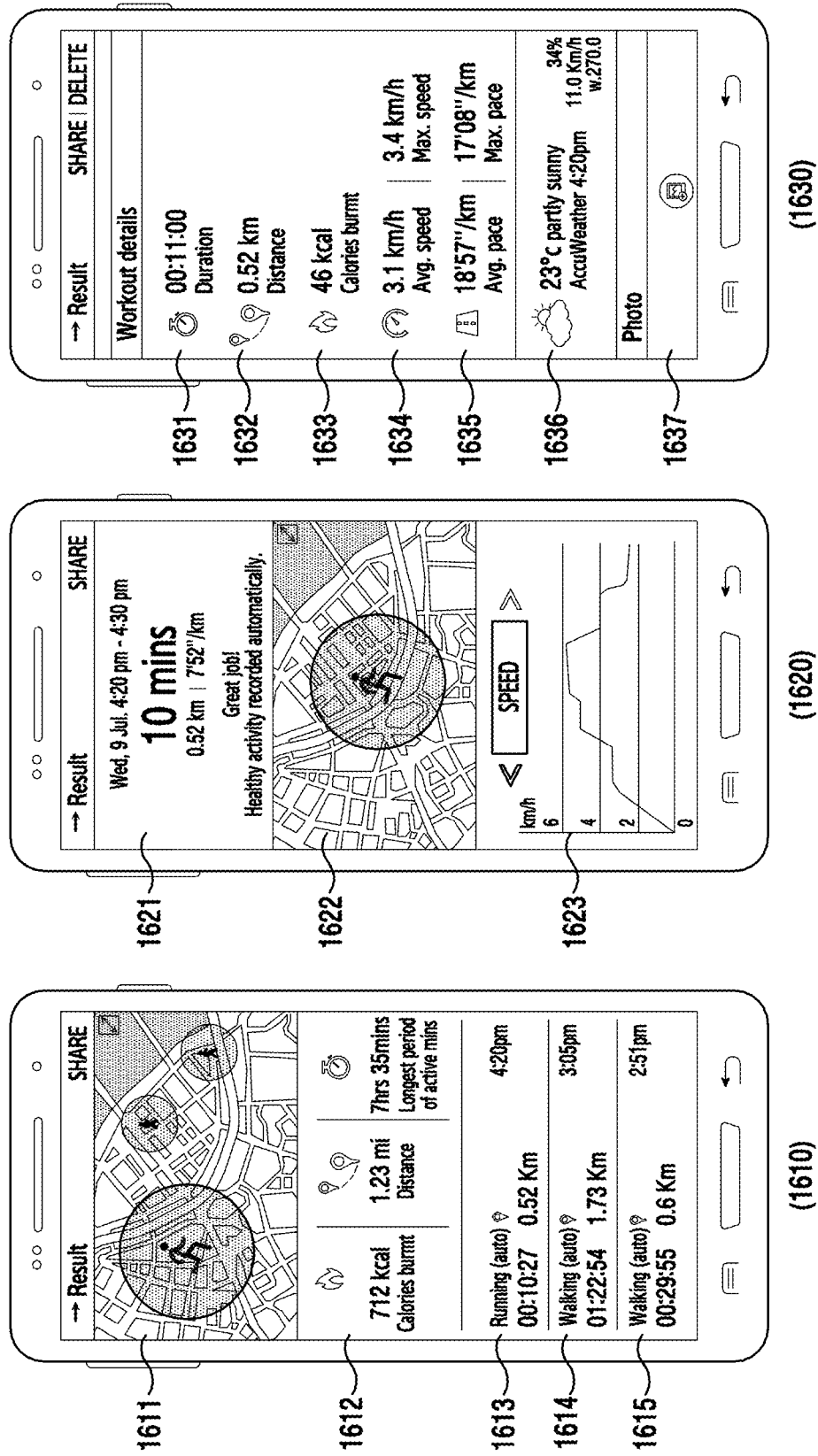
FIG. 16 illustrates an example of a user interface for activity information according to various embodiments.

FIG. 16 illustrates an example of a user interface for activity information according to various embodiments.

A user interface of FIG. 16 may be a user interface provided in operation 807 of FIG. 8. Referring to FIG. 16, the processor 120 may display a first user interface 1610 based on the corrected data. As an example, the first user interface 1610 may include a map image 1611 displaying activity areas for walking and activity information, integrated information 1612 for consumed calories, moved distance, the longest period of active times, and activity information on running 1613, walking 1 1614, and walking 2 1615 in a time sequence. For the corrected data, the processor 120 may include a tag (e.g., auto) in the activity information on the running 1613, the walking 1 1614, and the walking 2 1615. Alternatively, when the data is corrected based on the priority, the processor 120 may shade the item color for the corrected data. For example, the processor 120 may differently display the item colors of the corrected data and the uncorrected data.

The first user interface 1610 according to various embodiments may display such that at least one of the images, text, or symbols, associated with the corrected data, is overlapped in a map associated with locations that have been occupied for a predetermined time period. For example, the first user interface 1610 may display, on the map, data associated with the activity information, as icons, text, and the like.

According to various embodiments, the processor 120 may display a second user interface 1620 based on the corrected data. When a user selects one of the activity information on the running 1613, walking 1 1614, and walking 2 1615 through the first user interface 1610, the processor 120 may display the second user interface 1620. For example, when the user selects activity information on the running 1613 through the first user interface 1610, the processor 120 may display the second user interface 1620 that includes brief information 1621 indicating the time and distance for the running, a map image 1622 indicating the running area on the map, and a graph 1623 indicating the running speed.

According to various embodiments, the processor 120 may display a third user interface 1630 based on the corrected data. When the user selects one of the activity information on the running 1613, walking 1 1614, and walking 2 1615 through the first user interface 1610, the processor 120 may display the third user interface 1630. For example, when the user selects activity information on the running 1613 through the first user interface 1610, the processor 120 may display the third user interface 1630 that includes a duration 1631 and distance 1632 for the running, an amount of calories consumed by the running 1633, speed information 1634, pace information 1635, weather information 1636, and a photo button 1637.

The speed information 1634 may include an average speed and a maximum speed according to the time of the running. The pace information 1635 may include an average stride (pace) and a maximum pace according to the distance of the running. The weather information 1636 may include at least one of a weather icon, temperature, a weather type (e.g., clear, cloudy, rain, etc.), humidity, and wind direction. When the user selects a photo button 1637, the processor 120 may execute the camera. When the camera is executed, a camera application is executed and a preview image photographed by the camera may be displayed on the screen of the display 160.

Figure 17:
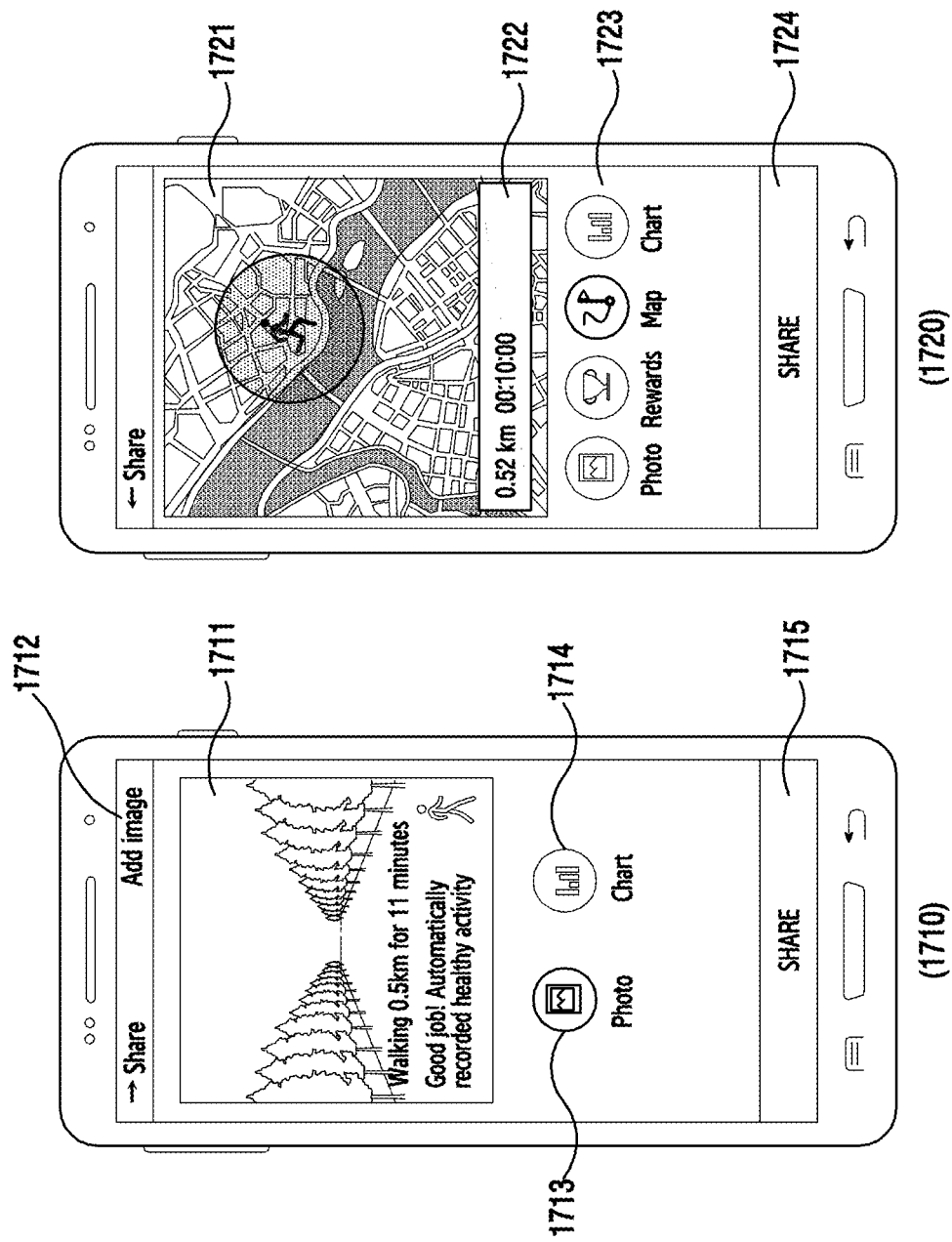
FIG. 17 illustrates an example of a user interface for sharing activity information according to various embodiments.

FIG. 17 illustrates an example of a user interface for sharing activity information according to various embodiments.

Referring to FIG. 17, the processor 120 may display a first user interface 1710 for sharing the activity information. For example, when a health-related application is input, selected by a user, the processor 120 may display a first user interface 1710 through the selected application. The health-related application may be installed in the electronic device 101 by a default value even without the user's request. Alternatively, the health-related application may be installed in the electronic device 101 at the request of the user. The first user interface 1710 may be the first screen after executing the application, or may be provided when the user selects 'share' in order to share activity information. For example, when activity information on the walking 1 1614 is selected through the first user interface 1610 of FIG. 16, the processor 120 may display a first user interface 1710.

The first user interface 1710 may include an image 1711, an image add button 1712, a photo button 1713, a chart view button 1714, and a share button 1715. The image 1711 may have been photographed by a user or already registered in an application. When the image add button 1712 is selected, a gallery application including the photographed photos may be executed. Alternatively, when the image add button 1712 is selected, various pop-up menus such as (1) camera execution, (2) gallery execution, and (3) cancellation may be displayed. When the photo button 1713 is selected, a camera application is executed and a preview image photographed by the camera may be displayed on the screen of the display 160. The chart view button 1714 may display detailed information including a map image, a moved distance, a speed, and the like for the activity information displayed on the image 1711. When the share button 1715 is selected, a menu for sharing the activity information displayed on the image 1711 with other users may be displayed. The menu for sharing may be a list of applications (e.g., message, e-mail, etc.) for sharing or a list of partner information (e.g., name, phone number, etc.) included in the contact list.

The processor 120 may display a second user interface 1720 for sharing the activity information. For example, when activity information on the running 1613 is selected through the first user interface 1610 of FIG. 16, the processor 120 may display the second user interface 1720. The second user interface 1720 may include a map image 1721, activity information 1722, a menu list 1723 such as photo, rewards, map view, and chart view, and a share button 1724. The map image 1721 may be a map that designates activity information on the running 1613 as an activity area on the map. The activity information 1722 may include the distance and time for the running 1613. When an item included in the menu list 1723 is selected, a screen for the corresponding item may be displayed. When the share button 1724 is selected, a menu for sharing the activity information displayed on the map image 1721 with other users may be displayed, similarly to the share button 1715.

Figure 18:
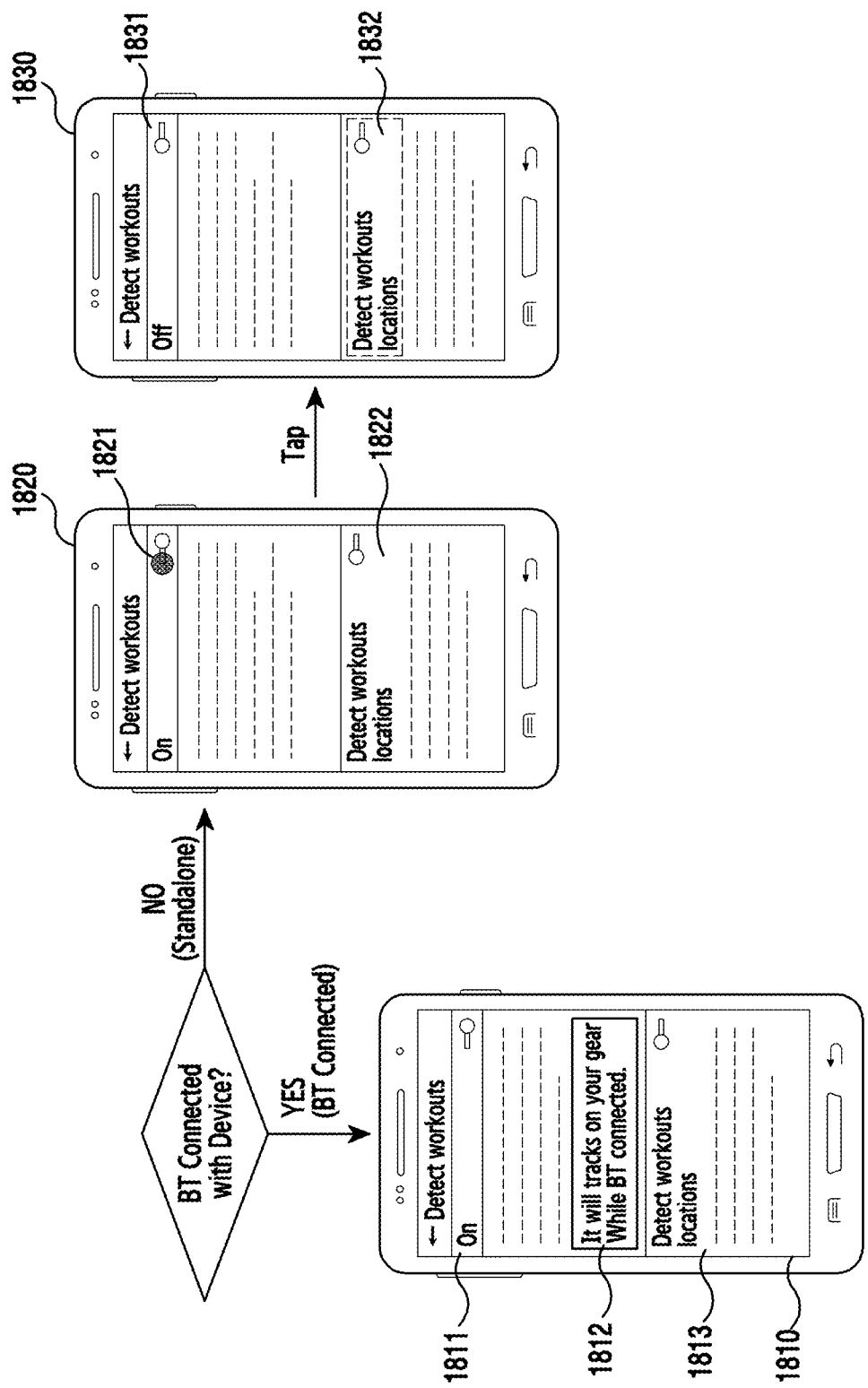
FIG. 18 illustrates an example of a user interface for configuring a recognition priority of a wearable device according to various embodiments.

FIG. 18 illustrates an example of a user interface for configuring a recognition priority of a wearable device according to various embodiments.

Referring to FIG. 18, when currently being connected with a device, the processor 120 may display a first user interface 1810 for configuring a recognition priority. The first user interface 1810 may include a recognition on/off item 1811 for configuring such that the currently connected device is preferentially recognized, a connection guide message 1812 generated according to turning on the on/off item 1811, and a location on/off item 1813 for configuring location information on the currently connected device. When the location on/off item 1813 is turned on, the processor 120 may collect location information on the currently connected device.

When currently not being connected with a device, the processor 120 may display a second user interface 1820 for configuring a recognition priority. The second user interface 1820 may include a recognition on/off item 1821 and a location on/off item (1822) for one of the currently unconnected devices (e.g., the first device) or a device (e.g., the first device) selected by a user among a list of devices. The second user interface 1820 may be configured such that the recognition on/off item 1811 is ON and the location on/off item 1822 is OFF. In order to protect the personal information of a user, the location on/off item 1822 may generally be turned OFF.

When the second user interface 1820 receives an input of selecting OFF of the recognition on/off item 1821 by a user, the processor 120 may display a third user interface 1830. The third user interface 1830 may be configured such that a recognition on/off item 1831 is OFF and a location on/off item 1822 is OFF. For example, when the touch input to the recognition on/off item 1821 by the user or the user input for changing the ON state configured in the recognition on/off item 1821 to the OFF state is generated, the processor 120 may display the third user interface 1830. The user input for changing the ON state to the OFF state may be a drag input for moving the touched location to the OFF direction after touching ON.

Figure 19:
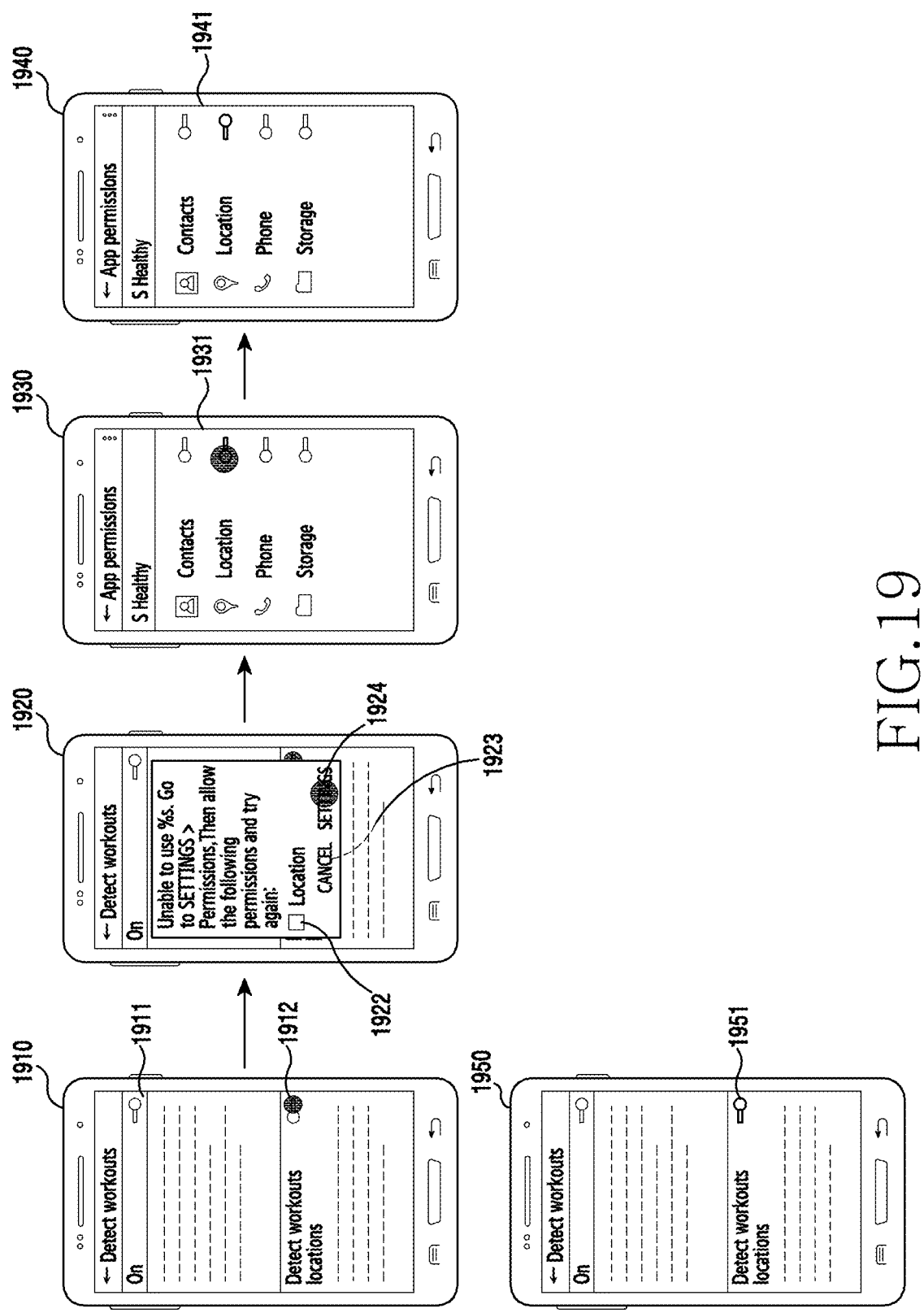
FIG. 19 illustrates an example of a user interface for configuring location information according to various embodiments.

FIG. 19 illustrates an example of a user interface for configuring location information according to various embodiments.

Referring to FIG. 19, the processor 120 may display a first user interface 1910. The first user interface 1910 may be similar to the second user interface 1820 of FIG. 18. For example, the first user interface 1910 may be configured such that a recognition on/off item 1911 is ON and a location on/off item 1912 is OFF. When the first user interface 1910 receives an input of selecting ON of the location on/off item 1912 by a user, the processor 120 may display a second user interface 1920.

The second user interface 1920 may be configured such that the first user interface 1910 includes a pop-up message 1921 thereon. The pop-up message 1921 may include, a notification message indicating the entrance to the setting menu of the electronic device 101, in order to change the setting to provide the location information, a location setting 1922, a cancel button 1923, and a setting button 1924. The location setting 1922 may be provided in a form of a check box. When the check box is checked (e.g., selected), the location setting 1922 is activated, and when the check box is not checked (e.g., not selected), the location setting 1922 may be deactivated.

When the search button 1924 is selected after selecting the location setting 1922, the processor 120 may display a third user interface 1930. The third user interface 1930 may be the one to be used for permission setting of the application of the electronic device 101. The third user interface 1930 may display various items (e.g., contacts, locations, phones, etc.) associated with the permission setting of the application. Generally, the electronic device 101 may be in an OFF state in order to protect the personal information of the user. That is, the location setting item 1931 of the third user interface 1930 may be in an OFF state.

When the location setting item 1931 is selected through the third user interface 1930, the processor 120 may provide a fourth user interface 1940. For example, when the touch input to the location setting item 1931 by the user or the user input for changing the OFF state configured in the location setting item 1931 to the ON state is generated, the processor 120 may display the fourth user interface 1940. The location setting item 1941 in the fourth user interface 1940 may be in an ON state.

When the user changes the location setting item 1941 and then selects OK, the processor 120 may provide a second user interface 1950. The second user interface 1950 may be configured such that a location on/off item 1951 is configured to ON in the first user interface 1910. When the location on/off item 1951 is turned on, the processor 120 may collect location information on a device associated with the second user interface 1950.

Figure 20:
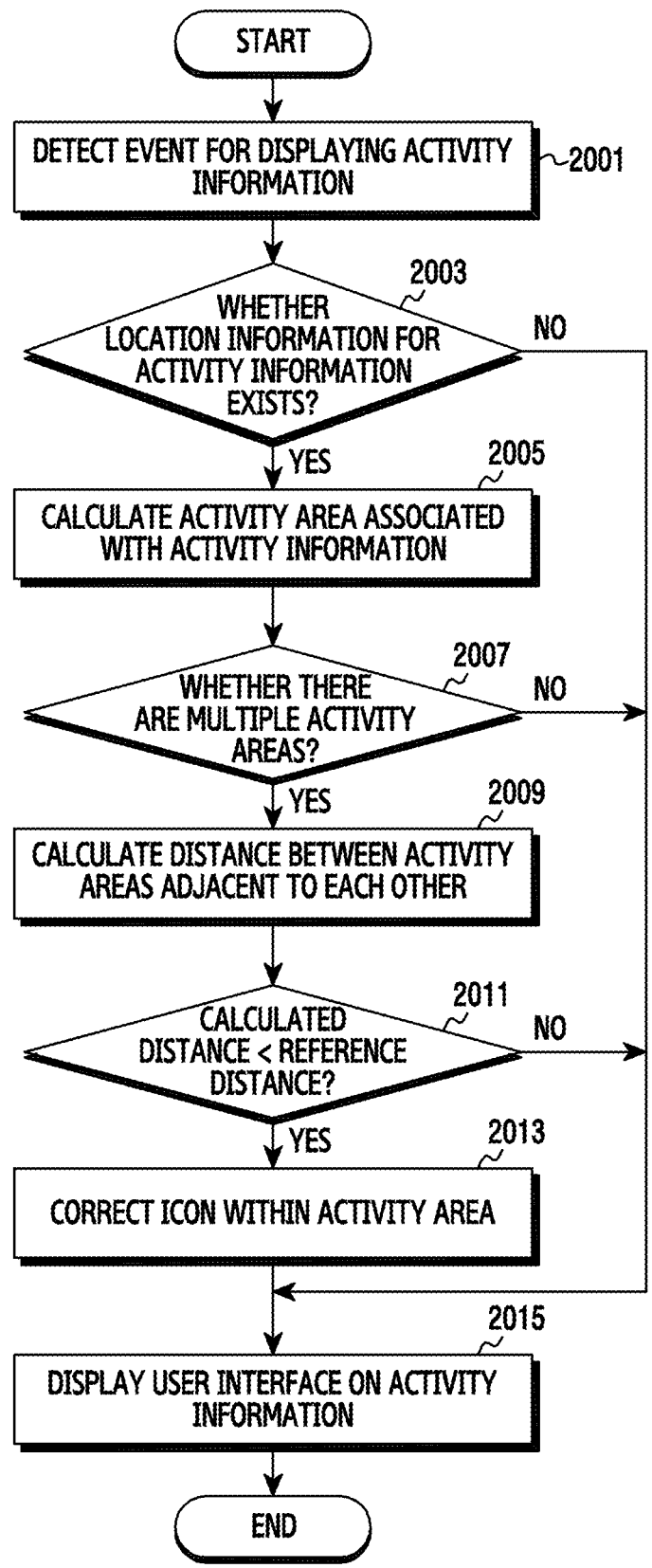
FIG. 20 illustrates a method for displaying a user interface by an electronic device according to various embodiments.

FIG. 20 illustrates a method for displaying a user interface by an electronic device according to various embodiments.

Referring to FIG. 20, in operation 2001, the electronic device 101 (e.g., the processor 120) may detect an event for displaying activity information. The event may be at least one of an application execution event displaying health related data, an event for selecting a map image through the application, and an event for selecting activity information through the application. The processor 120 may provide a user interface or user experience associated with the activity information in response to the detected event. For example, the processor 120 may display the user interface (e.g., 1610 and 1620) of FIG. 16 in response to the detected event.

In operation 2003, the electronic device 101 (for example, the processor 120) may determine whether the location information for the activity information exists. When the location information associated with the activity information exists, the processor 120 may display an activity area for activity information based on the location information. However, when the location information associated with the activity information does not exist, the processor 120 may not display an activity area associated with the activity information on the map.

The processor 120 may perform an operation 2005 when the location information on the activity information exists, and perform an operation 2015 when the location information on the activity information does not exist.

In operation 2005, the electronic device 101 (for example, the processor 120) may calculate the activity area associated with the activity information. The processor 120 may or may not provide location information for each device. In addition, even when the location information is provided, the sampling rate for the location information may be different for each device. Accordingly, the processor 120 may represent the activity area in a circular form in order to provide a user interface. For example, when one piece of location information exists for one piece of activity information, the processor 120 may calculate an activity area having a predetermined radius with reference to location information. The predetermined radius may be configured by the user or configured to the electronic device 101 by a default value. When two pieces of location information exist for one piece of activity information, the processor 120 may calculate the center point using two end points.

The processor 120 may calculate the center point using the average method as shown in Equation 2.

$$\text{center } (a, b) = \left(\frac{a_x + b_x}{2}, \frac{a_y + b_y}{2}\right) \quad [\text{Equation 2}]$$

Center (a, b) may be the coordinates of the center point, $a_x$ and $a_y$ are the coordinates of the first end point, and $b_x$ and $b_y$ are the coordinates of the second end point.

The processor 120 may calculate an activity area for activity information extracted from each device.

In operation 2007, the electronic device 101 (for example, the processor 120) may determine whether there are multiple activity areas. For example, the processor 120 may provide activity information detected in one or more devices, and when there are multiple activity areas, the active areas may overlap with each other.

When there are multiple active areas, the processor 120 may perform an operation 2009, and when the active areas are not multiple, the processor 120 may perform an operation 2015.

In operation 2009, the electronic device 101 (for example, the processor 120) may calculate the distance between activity areas adjacent to each other. For example, the processor 120 may calculate the distance between the activity areas using the distance between center points of activity areas.

The processor 120 may calculate the distance between two activity areas as shown in Equation 3.

$$\text{dist}(a,b) = \sqrt{(a_x - b_x)^2 + (a_y - b_y)^2} \quad [\text{Equation 3}]$$

dist (a, b) may be the distance between two activity areas, $a_x$ and $a_y$ may be the center coordinates of the first activity area, and $b_x$, $b_y$ may be the center coordinates of the second activity area.

The processor 120 may calculate the distance between two activity areas using the Euclidean distance of Equation 3, and determine whether the two activity areas overlap with each other, using the calculated distance.

In operation 2011, the electronic device 101 (for example, the processor 120) may determine whether the calculated distance is less than a reference distance. The reference distance may be configured by the user or the electronic device 101.

The processor 120 may determine whether two activity areas are overlapped with each other as shown in Equation 4.

$$\text{dist}(a,b) < \alpha \times (\text{radius of icon}_1 + \text{radius of icon}_2) \quad [\text{Equation 4}]$$

dist (a, b) may be the distance between two activity areas, $\alpha$ may be the reference distance, radius of $\text{icon}_1$ may be the center point (or icon) of the first activity area, and radius of icon, may be the center point (or icon) of the second activity area.

For example, when the condition obtained by Equation 4 is true, the processor 120 may perform an overlap control process. For example, when the reference distance (e.g., alpha (a)) is 1, an overlap control process between two activity areas may be performed. When the reference distance is greater than 1, the two activity areas may not overlap with each other, and when the reference distance is less than 1, the two activity areas may overlap by a predetermined size or more.

According to various embodiments, the processor 120 may configure the reference distance based on a map ratio of a map image where the active area is to be displayed, and based on the size of the activity area. For example, when the map ratio is increased or decreased, the size of the activity area may be increased or decreased. Alternatively, when the map ratio is increased or decreased, the size of the activity area may be decreased or increased. The map ratio and the size of the activity area may be proportional or inversely proportional to each other. According to various embodiments, when the size of the activity area is changed according to the map ratio, the processor 120 may adjust the reference distance according to the map ratio and the size of the activity area.

The processor 120 may perform an operation 2013 when the calculated distance is less than the reference distance, and may perform an operation 2015 when the calculated distance is equal to or greater than the reference distance.

In operation 2013, the electronic device 101 (for example, the processor 120) may correct an icon within the activity area.

According to various embodiments, the processor 120 may place a priority on the activity areas in order to prevent as much as possible the case where activity areas on activity information extracted from the plurality of devices are overlapped to each other, thereby reducing the overlapping of the activity areas. The priority may be configured to at least one of a radius of the activity area, a workout type, and a device. The priority may be configured by the user or the electronic device 101. A device which can be processed using a duplicated function and a device which cannot be processed in duplicates may be distinguished and displayed according to the priority. For example, the device that cannot be processed in duplicates may be shaded and then provided. To this end, the processor 120 may perform the following operations.

For example, when the radius of the activity area has a priority, the processor 120 may configure the priority in the descending order by the magnitude of the radius of the activity area, maintain icons in the activity area which has a higher priority, and delete icons in an activity area which has a lower priority. When the workout type has a priority, the processor 120 may maintain the icon in the activity area based on a workout type having a higher priority, and delete the icon in the activity area of the workout type having a lower priority. When a device has a priority, the processor 120 may maintain icons in the activity area based on the activity information extracted from the device having a higher priority, and delete icons in the activity area extracted a device having a lower priority.

In operation 2015, the electronic device 101 (for example, the processor 120) may display a user interface for the activity information. When the operation 2015 is performed during the operation 2005 and operation 2007, the processor 120 may display the user interface for the activity information without correcting icons in the activity area associated with the activity information. When the operation 2013 is performed and then the operation 2015 is performed, the processor 120 may display a user interface for activity information on which the icons have corrected. For example, the processor 120 may display the user interface (e.g., 1610 and 1620) of FIG. 16 as the user interface for the activity information.

Figure 21:
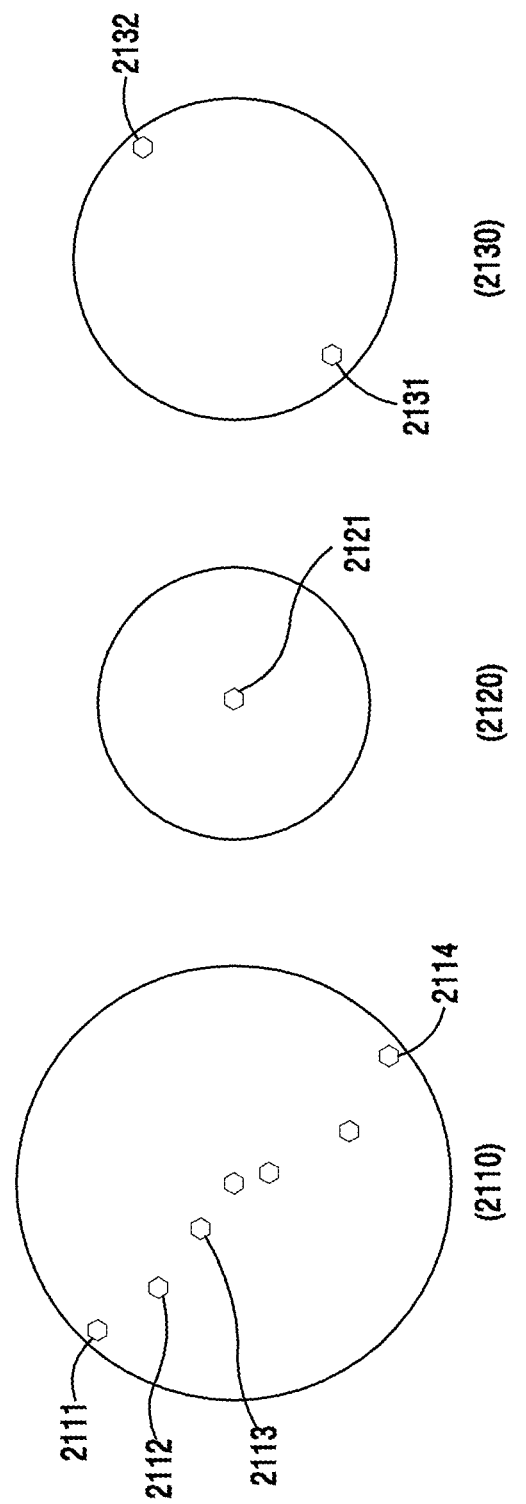
FIG. 21 illustrates an example of calculating an active area according to various embodiments.

FIG. 21 illustrates an example of calculating an activity area according to various embodiments.

Referring to FIG. 21, the processor 120 may calculate an activity area based on location information. When a plurality of pieces of location information (e.g., 2111, 2112, 2113, and 2114) for the activity information exist, the processor 120 may calculate the center point using two end points (e.g., 2111 and 2114). The processor 120 may calculate the activity area 2110 using the calculated center point. In addition, when one piece of location information (e.g., 2121) exists for one piece of activity information, the processor 120 may calculate an activity area 2120 which has a predetermined radius with reference to location information. In addition, when two pieces of location information exist, the processor 120 may calculate the center point using two pieces of location information (e.g., 2132 and 2132). The processor 120 may calculate the activity area 2130 using the calculated center point.

FIG. 22A to FIG. 24B illustrate examples of correcting an icon in an activity area based on a threshold according to various embodiments.

FIGS. 22A to 22D show an example of correcting an icon in an activity area when the threshold is small.

Figure 22A:
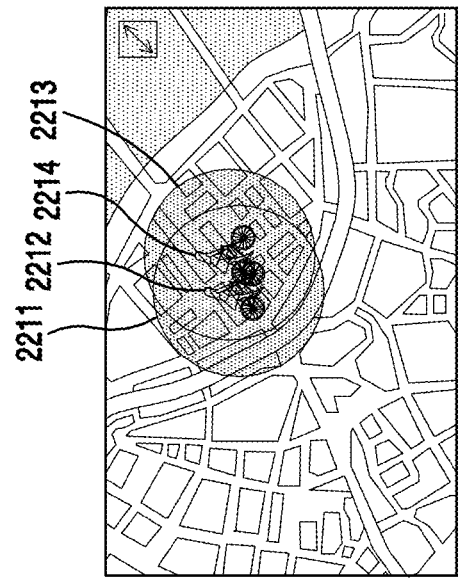
Figure 22B:
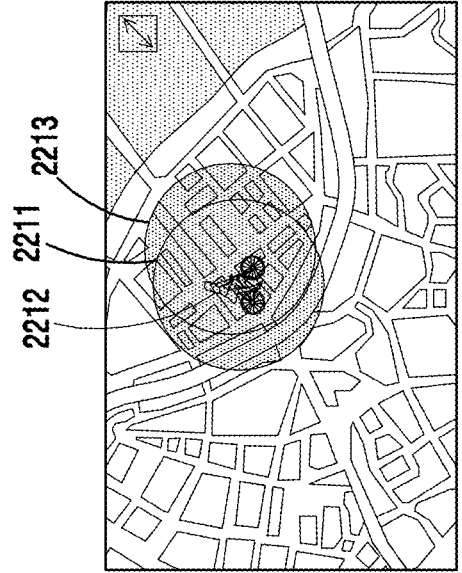
Figure 22C:
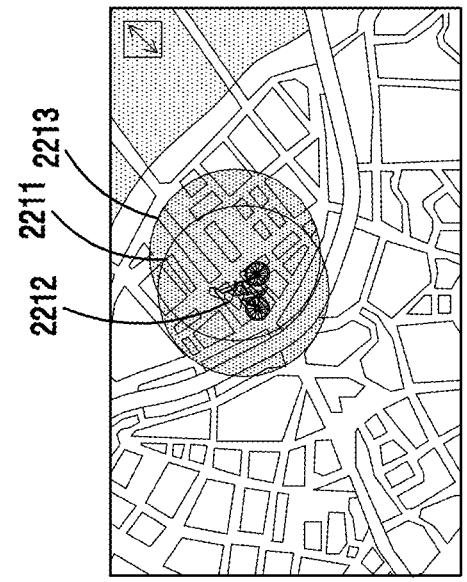
Figure 22D:
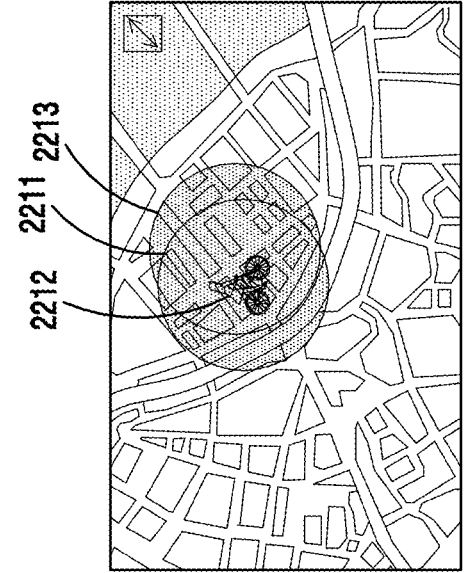

FIG. 22A shows activity areas (e.g., 2211, 2213) for activity information before the overlapped icons are corrected. Referring to FIG. 22A, a first icon 2212 may be displayed in a first activity area 2211, and a second icon 2214 may be displayed in a second activity area 2213. The processor 120 may perform an icon overlapping process by applying different overlapping ratios to activity areas as shown in FIG. 22A. FIG. 22B shows an example in which the icon overlapping process is performed by lowering the overlapping ratio. FIG. 22C shows an example in which the icon overlapping process is performed by making the overlapping ratio to a medium ratio. FIG. 22D shows an example in which the icon overlapping process is performed by increasing (e.g., high) the overlapping ratio. Referring to FIG. 22B to FIG. 22D, the first icon 2212 included in the first activity area 2211 may be displayed, and the second icon 2214 displayed in the second activity area 2213 may be deleted. That is, when the threshold is small, it can be seen that the second icon 2214 displayed in the second activity area 2213 is deleted even if the overlapping ratio is differently configured.

FIGS. 23A to 23D show another example of correcting an icon in an activity area when the threshold is small.

Figure 23A:
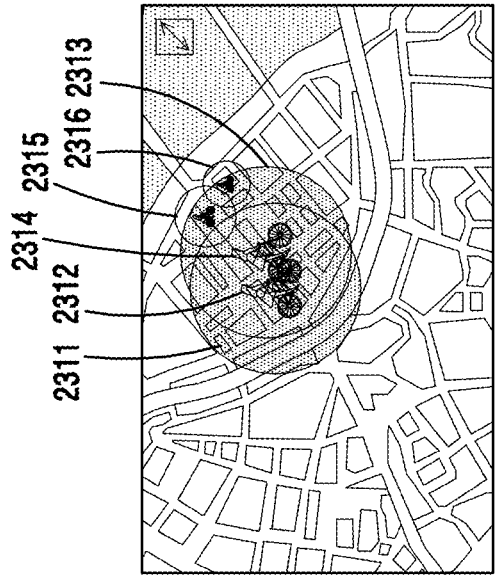
Figure 23B:
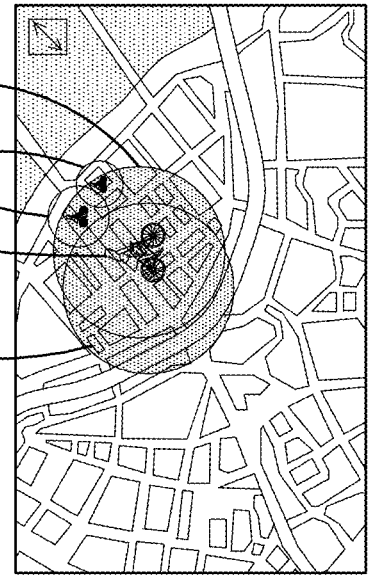

FIG. 23A shows activity areas for activity information before the overlapped icons are corrected. Referring to FIG. 23A, a first icon 2312 may be displayed in a first activity area 2311, and a second icon 2314 may be displayed in a second activity area 2313. Icons may also be displayed in a third activity area 2315 and a fourth activity area 2316, respectively. The processor 120 may perform an icon overlapping process by applying different overlapping ratios to the activity areas as shown in FIG. 23A. FIG. 23B shows an example in which the icon overlapping process is performed by lowering the overlapping ratio. When the overlapping ratio is configured to be low, as shown in FIG. 23B, the first icon 2312 may be displayed in the first activity area 2311, and the second icon 2314 may be displayed in the second activity area 2313, as shown in FIG. 23A. Icons may also be displayed in the third activity area 2315 and the fourth activity area 2316, respectively.

Figure 23C:
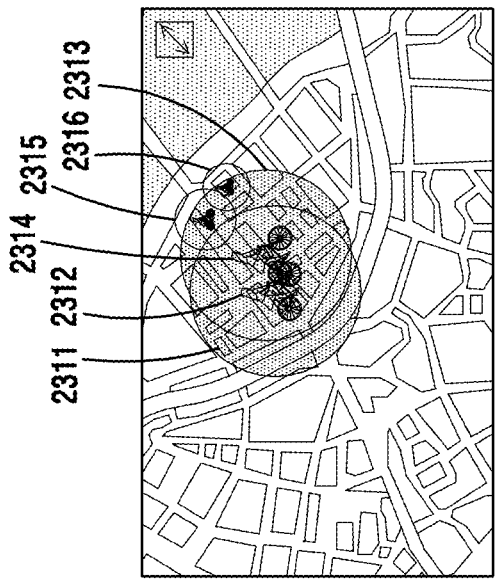
Figure 23D:
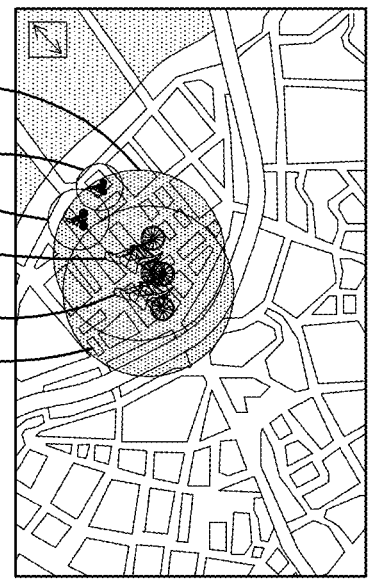

FIG. 23C shows an example in which the icon overlapping process is performed by making the overlapping ratio to a medium ratio. FIG. 23D shows an example in which the icon overlapping process is performed by increasing (e.g., high) the overlapping ratio. Referring to FIG. 23C to FIG. 23D, the first icon 2312 displayed in the first activity area 2311 may be deleted, the second icon 2314 may be displayed in the second active area 2313, and icons may also be displayed in the third activity area 2315 and the fourth activity area 2316, respectively.

Therefore, if the threshold is small, the icon may not be deleted even if the icon overlapping process is performed.

Figures 24A, 24B:
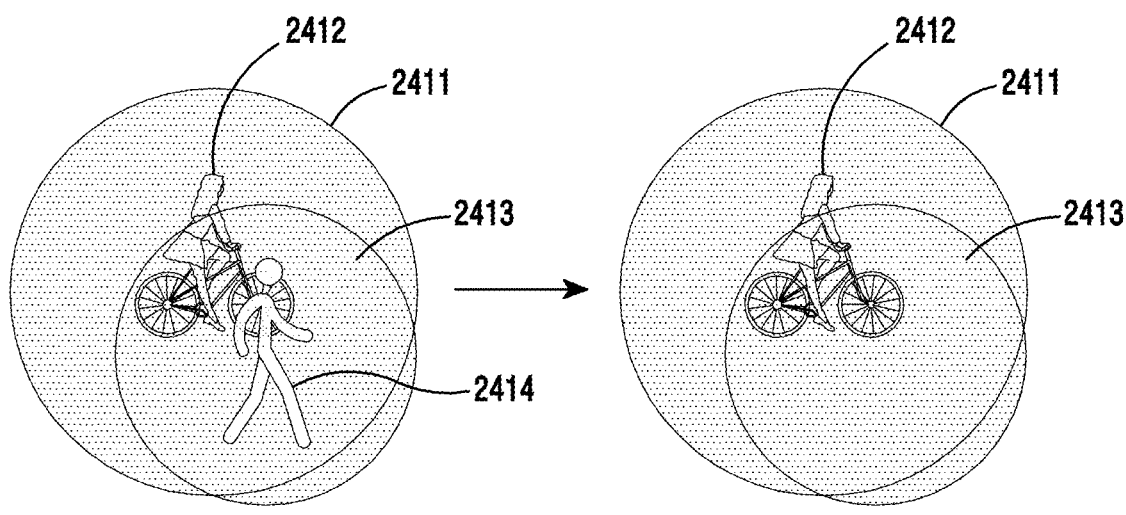

FIGS. 24A and 24B illustrate an example of correcting an icon in an activity area when the threshold is high.

Referring to FIG. 24A shows activity areas for activity information before the overlapped icons are corrected. Referring to FIG. 24A, a first icon 2412 may be displayed in a first activity area 2411, and a second icon 2414 may be displayed in a second activity area 2413. The processor 120 may perform the icon overlapping process by increasing the threshold. Referring to FIG. 24B, the first icon 2412 may be displayed in the first activity area 2411, and the second icon 2414 may be deleted in the second activity area 2413.

Accordingly, when the icon overlapping process is performed when the threshold is large, icons that should not be deleted may be deleted.

According to various embodiments, when performing the icon overlapping process, the processor 120 may weigh the importance of the icon (e.g., the priority of the workout type)

and the physical quantity for activity information, etc., so as to maintain an important icon, and delete an unimportant icon.

FIG. 25A to FIG. 26C illustrate examples of processing overlapped icons according to various embodiments.

Figure 25A:
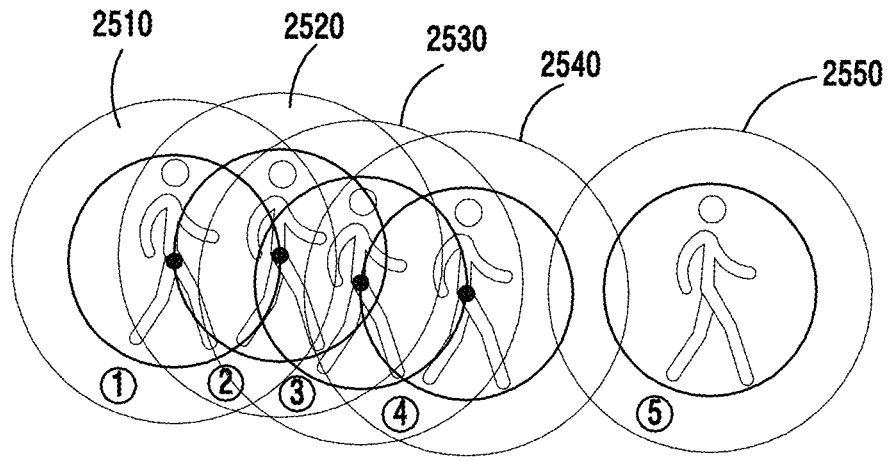
FIG. 25A to FIG. 26C illustrate an example of processing overlapped icons according to various embodiments.
Figure 25B:
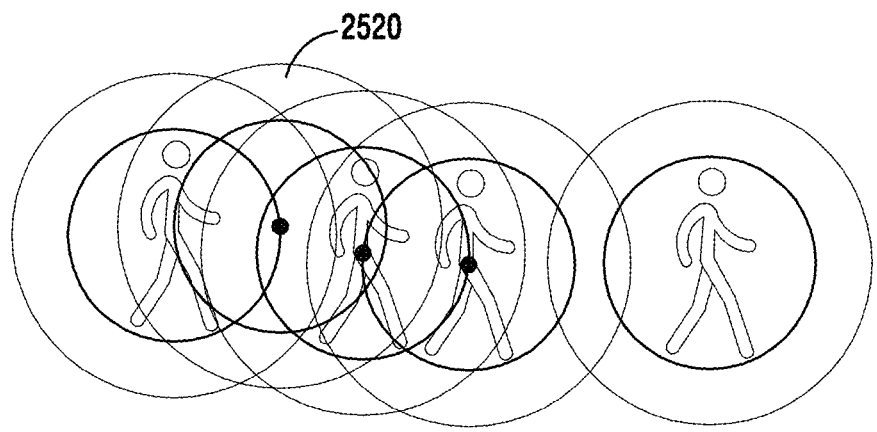
Figure 25C:
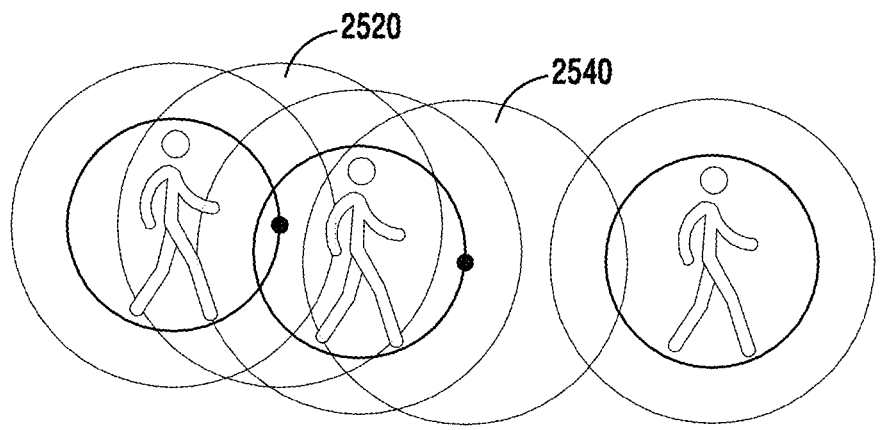

FIGS. 25A to 25C illustrate an example of processing an overlapped icon using a greedy set cover. The greedy set cover (Chvatal, V.: A Greedy Heuristic for the Set-Covering Problem. Math. of Oper. Res., Vol. 4, 1979, No. 3, pp. 233-235) may be one of the methods of processing an overlapped icon.

Referring to FIGS. 25A to 25C, the processor 120 may display each icon in a first activity area 2510, a second activity area 2520, a third activity area 2530, a fourth activity area 2540, and a fifth activity area 2550, as shown in FIG. 25A. For example, the processor 120 may display each activity area in a time sequence, as shown in FIG. 25A, if the icons are not prioritized. An icon for each activity area may be configured to 1, 2, 3, 4, and 5 in order. The initial set { } may be an empty state, and become {1} and {1, 2} in order, and icons 1 and 2 may satisfy the overlapping condition.

The overlapping condition is described in operation 2111 described above, and when the center point distance between the first activity area 2510 and the second activity area 2520 including the icons 1 and 2 is smaller than the reference distance, the processor 120 may determine that the overlapping condition is satisfied. Since the icons 1 and 2 satisfy the overlapping condition, the processor 120 may delete the icon 2. That is, the processor 120 may delete the icon included in the second activity area 2520 as shown in FIG. 25B.

Then, since the icon 2 has been deleted, when adding the icon 3 in a state of {1}, the processor 120 may configure set {1, 3}, and determine the overlapping condition between the icons 1 and 3. Since the overlapping condition is not satisfied between the icons 1 and 3, the processor 120 may configure a set {1, 3, 4} by successively adding an icon 4. Icons 3 and 4 included in the third activity area 2530 and the fourth activity area 2540, which are two adjacent activity areas, may satisfy the overlapping condition. In this case, the processor 120 may delete the icon included in the fourth activity area 2540 as shown in FIG. 25C. Since the icon 4 is deleted, the processor 120 may configure a set {1, 3, 5} by adding an icon 5 in the state of set {1, 3}, and determine the overlapping condition between the icons 3 and 5. Since the icons 3 and 5 do not satisfy the overlapping condition, the processor 120 may terminate the icon overlapping process.

In FIG. 25C, which has completed the icon overlapping process, only icons for the first activity area 2510, the third activity area 2530, and the fifth activity area 2550 may be maintained, and the icons for the second activity area 2520 and the fourth activity area 2540 may be deleted. The processor 120 may display a user interface that includes activity information as shown in FIG. 25C, in operation 1215.

The processor 120 according to various embodiments may assign a priority to at least one of a radius of an activity area, an workout type, and a device.

Figure 26A:
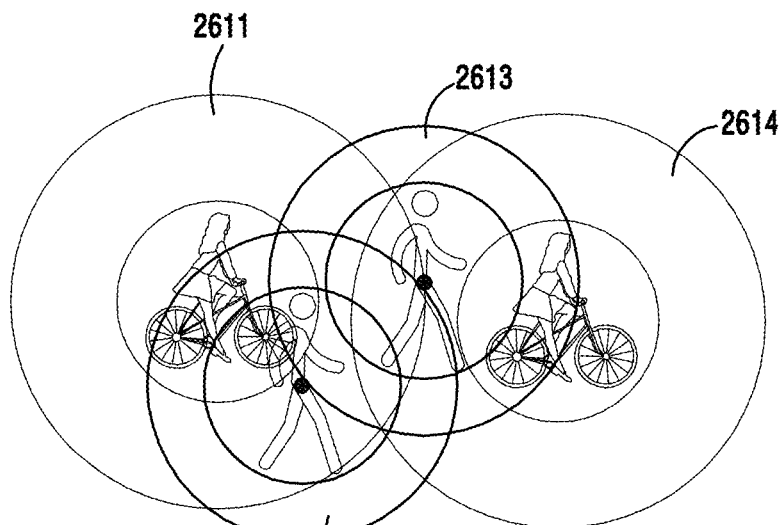
Figure 26B:
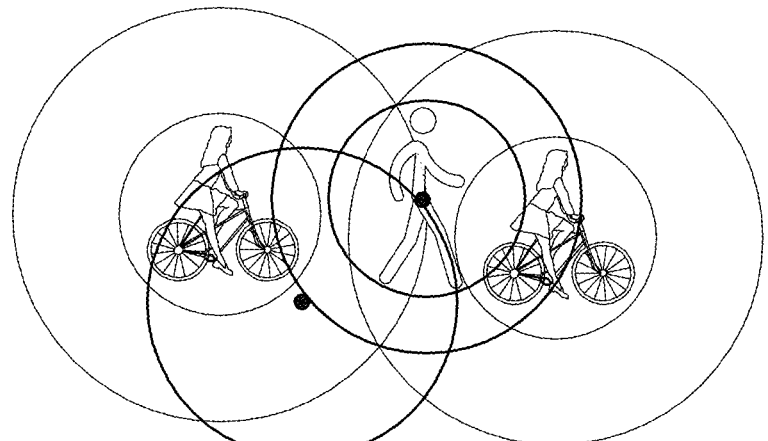
Figure 26C:
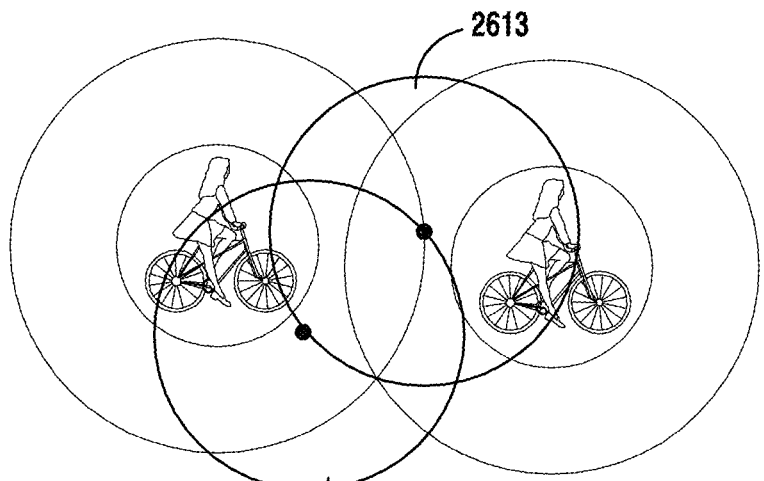

FIGS. 26A to 26C illustrate an example of processing overlapped icons by placing a priority on workout types.

Referring to FIGS. 26A to 26C, the processor 120 may display each icon in a first activity area 2611, a second activity area 2612, a third activity area 2613, and a fourth activity area 2614, as shown in FIG. 26A. For example, the first activity area 2611 and the fourth activity area 2614 may correspond to the activity information when the workout type is 'cycling', and the second activity area 2612 and the third activity area 2613 may correspond to the activity information when the type of workout is 'walking'.

The processor 120 may configure the set in the sequence of higher priorities and apply the greedy set cover to the same. An icon for each activity area may be configured to 1, 2, 3, and 4 in order. The initial set { } may be an empty state, become {1} and {1, 4} in the sequence of higher priorities, and icons 1 and 4 may not satisfy the overlapping condition. That is, since the icons of the first activity area 2611 and the fourth activity area 2614 do not overlap each other, the processor 120 may successively add an icon 2 to configure a set {1, 4, 2}. Icons 4 and 2 included in the fourth activity area 2614 and the second activity area 2612, which are two adjacent activity areas, may satisfy the overlapping condition. In this case, the processor 120 may delete the icon included in the second activity area 2612 as shown in FIG. 26B. The icon 2 is deleted based on the priority without deleting icon 4.

Since the icon 2 is deleted, the processor 120 may configure a set {1, 4, 3} by adding the icon 3 in a state of set {1, 4}, and determine the overlapping condition between the icons 4 and 3. Since the icons 4 and 3 satisfy the overlapping condition, the processor 120 may delete the icon included in the third activity area 2613, as shown in FIG. 26C. The icon 3 is deleted based on the priority without deleting icon 4. Since the activity area to be included in the set does not exist anymore after performing the above process, the processor 120 may terminate the icon overlapping process. In FIG. 26C, which has completed the icon overlapping process, only icons for the first activity area 2611 and the fourth activity area 2614 may be maintained, and icons for the second activity area 2612 and the third activity area 2613 may be deleted.

In this manner, the processor 120 may perform an icon overlapping process using a greedy set cover and a threshold, so as to provide a user with an activity area in which icons are not overlapped.

An operation method for an electronic device according to various embodiments may include operations of: acquiring health related data; correcting the acquired data per unit time; extracting activity information by analyzing the corrected data; and displaying a user interface including the activity information in response to a user request.

The operation of correcting the acquired data may include an operation of correcting the acquired data based on a time unit for storing data of the electronic device.

The operation of extracting the activity information may include an operation of: analyzing data acquired from an external device and data acquired by using the sensor module of the electronic device, so as to classify the data depending on an activity type; and integrating the data depending on the activity type.

The data integration operation may include an operation of integrating data based on a priority of at least one of a time, an activity type, a workout type, and a device.

The operation method may further include operations of: assigning different weights to at least one of the activity type, the workout type, and the device; and correcting the integrated data based on the weights.

The operation method may further include operations of: classifying the number of steps for each device per unit time; determining the maximum number of steps per unit time; and calculating the integrated number of steps based on the determined maximum number of steps.

The operation method may further include operations of: determining a workout type based on the result of data analysis; determining the start and end of the workout type; and integrating activity information for each workout type based on the priority.

The operation method may further include operations of: aligning inactive intervals for each time; and integrating inactive intervals that do not include the activity information into one session, so as to process the integrated session as non-activity information.

The displaying operation may include operations of: extracting location information for the activity information; calculating an activity area for the activity information based on the extracted location information; calculating a distance between two adjacent activity areas; correcting an icon in an activity area based on the calculated distance; and displaying a user interface including the corrected icon.

The operation of correcting the icon may include operations of: determining such that the icon overlap condition is satisfied when the calculated distance is less than a reference distance; and deleting at least one of icons included in the adjacent two active areas.

A computer-readable recording media can include a hard disk, a floppy disk, a magnetic media (e.g., a magnetic tape), an optical media (e.g., a Compact Disc-Read Only Memory (CD-ROM) and/or Digital Versatile Disk (DVD)), a Magneto-Optical Media (e.g., a floptical disk), an internal memory, etc. An instruction can include a code made by a compiler or a code executable by an interpreter. A module or a program module according to various exemplary embodiments can further include at least one or more of the aforementioned constituent elements, or omit some, or further include another constituent element. Operations carried out by a module, a program module or another constituent element according to various exemplary embodiments can be executed in a sequential, parallel, repeated or heuristic method, or at least some operations can be executed in different order or can be omitted, or another operation can be added.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An electronic device comprising:
a housing;
a display exposed through a part of the housing;
a first motion sensor disposed within the housing and configured to detect movement of the housing;
a wireless communication circuit disposed within the housing;
a processor disposed within the housing and electrically connected to the display, the first motion sensor, and the wireless communication circuit; and
a memory electrically connected to the processor, wherein the memory stores instructions that, when executed by the processor, cause the processor to:
establish, using the wireless communication circuit, a wireless communication channel with an external electronic device that includes a second motion sensor;
obtain first data regarding the movement of the housing by using the first motion sensor for a first time period;
receive second data regarding a movement of the external electronic device obtained by the second motion sensor of the external electronic device for the first time period through the wireless communication channel;
identify a first user activity type indicated by the first data;
identify a second user activity type indicated by the second data;
determine the first user activity type indicated by the first data is different from the second user activity type indicated by the second data;
based on the determination that the first user activity type is different from the second user activity type, select one of the first user activity type or the second user activity type based on a designated priority; and
based on the selection, recognize an activity performed by a user for the first time period as the selected user activity type.

2. The electronic device of claim 1, wherein the instructions, when executed by the processor, cause the processor to display at least one of an image, a text, or a symbol representing the recognized activity type.

3. The electronic device of claim 1, wherein identifying the first user activity type comprises:
determining a first attribute of the movement of the housing during a first session of the first time period using a first portion of the first data;
determining a second attribute of the movement of the housing during a second session of the first time period using a second portion of the first data;
identifying the first user activity type based on the first attribute and the second attribute; and
displaying at least one of an image, a text, or a symbol representing the identified first user activity type through a user interface displayed on the display.

4. The electronic device of claim 3, wherein the instructions, when executed by the processor, cause the processor to:
display, through the user interface, a map associated with locations where the housing has been located for the first time period, and
display at least one of the image, the text, or the symbol on the map in a superposed manner.

5. The electronic device of claim 1,
wherein the designated priority is allocated on at least one of an activity type, a workout type, a device, or a start time of an activity; and
wherein the selected user activity type includes walking, activity, and non-activity.

* * * * *